United States Patent
Trauth et al.

(10) Patent No.: US 9,890,177 B2
(45) Date of Patent: *Feb. 13, 2018

(54) NITRATED HYDROCARBONS, DERIVATIVES, AND PROCESSES FOR THEIR MANUFACTURE

(71) Applicant: ANGUS Chemical Company, Buffalo Grove, IL (US)

(72) Inventors: Daniel M. Trauth, Crystal Lake, IL (US); George D. Green, Cary, IL (US); Raymond J. Swedo, Mt. Prospect, IL (US); Richard L. James, Eros, LA (US); Ian A. Tomlinson, Midland, MI (US)

(73) Assignee: ANGUS CHEMICAL COMPANY, Buffalo Grove, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/920,156

(22) Filed: Oct. 22, 2015

(65) Prior Publication Data

US 2016/0039843 A1 Feb. 11, 2016

Related U.S. Application Data

(62) Division of application No. 12/934,817, filed as application No. PCT/US2009/039901 on Apr. 8, 2009, now Pat. No. 9,187,436.

(60) Provisional application No. 61/045,380, filed on Apr. 16, 2008.

(51) Int. Cl.

| | | |
|---|---|---|
| *C07D 498/10* | (2006.01) | |
| *A01N 43/76* | (2006.01) | |
| *A01N 43/90* | (2006.01) | |
| *C07C 201/08* | (2006.01) | |
| *C07C 201/12* | (2006.01) | |
| *C07C 205/02* | (2006.01) | |
| *C07C 205/06* | (2006.01) | |
| *C07C 205/18* | (2006.01) | |
| *C07C 215/08* | (2006.01) | |
| *C07C 215/42* | (2006.01) | |
| *C07C 239/10* | (2006.01) | |
| *C07D 263/04* | (2006.01) | |
| *C07D 263/52* | (2006.01) | |
| *C07D 498/04* | (2006.01) | |
| *C08G 18/32* | (2006.01) | |
| *C07C 205/04* | (2006.01) | |
| *C07C 205/05* | (2006.01) | |
| *C07C 205/15* | (2006.01) | |
| *C07C 205/16* | (2006.01) | |
| *C07C 215/20* | (2006.01) | |
| *C07C 215/28* | (2006.01) | |

(52) U.S. Cl.
CPC ........... *C07D 498/10* (2013.01); *A01N 43/76* (2013.01); *A01N 43/90* (2013.01); *C07C 201/08* (2013.01); *C07C 201/12* (2013.01); *C07C 205/02* (2013.01); *C07C 205/04* (2013.01); *C07C 205/05* (2013.01); *C07C 205/06* (2013.01); *C07C 205/15* (2013.01); *C07C 205/16* (2013.01); *C07C 205/18* (2013.01); *C07C 215/08* (2013.01); *C07C 215/20* (2013.01); *C07C 215/28* (2013.01); *C07C 215/42* (2013.01); *C07C 239/10* (2013.01); *C07D 263/04* (2013.01); *C07D 263/52* (2013.01); *C07D 498/04* (2013.01); *C08G 18/3271* (2013.01); *C07C 2601/08* (2017.05); *C07C 2601/14* (2017.05); *C07C 2601/18* (2017.05); *C07C 2602/10* (2017.05); *Y02P 20/582* (2015.11)

(58) Field of Classification Search
CPC ...... A01N 43/76; A01N 43/90; C07C 201/08; C07C 201/12; C07C 205/02; C07C 205/06; C07C 205/18; C07C 215/08; C07C 215/42; C07C 239/10; C07D 263/04; C07D 263/52; C07D 498/04
See application file for complete search history.

(56) References Cited

U.S. PATENT DOCUMENTS

| | | |
|---|---|---|
| 1,967,667 A | 7/1934 | Hass et al. |
| 2,139,121 A | 12/1938 | Hass et al. |
| 2,139,124 A | 12/1938 | Hass et al. |
| 2,489,320 A | 12/1949 | Nygaard et al. |
| 2,511,454 A | 3/1950 | Evans et al. |
| 3,066,173 A | 12/1962 | Lee et al. |
| 3,272,874 A | 9/1966 | Abbott et al. |
| 3,534,112 A | 10/1970 | Tindall |
| 3,564,057 A | 2/1971 | Tindall et al. |
| 3,780,115 A | 12/1973 | Lhonore et al. |
| 3,869,253 A | 3/1975 | Lhonore et al. |
| 3,917,705 A | 11/1975 | Swanson et al. |

(Continued)

FOREIGN PATENT DOCUMENTS

| | | | |
|---|---|---|---|
| CN | 101391964 | * | 3/2009 |
| DE | 19527121 | | 1/1997 |
| EP | 2 019 100 | | 1/2009 |
| GB | 1 245 469 | | 9/1971 |
| WO | WO-00/42079 | | 7/2000 |

OTHER PUBLICATIONS

Spielman et al., 1948, caplus an 1948:21363.*

(Continued)

*Primary Examiner* — Sun Jae Yoo
(74) *Attorney, Agent, or Firm* — Foley & Lardner LLP

(57) ABSTRACT

Provided is a process for the formation of nitrated compounds by the nitration of hydrocarbon compounds with dilute nitric acid. Also provided are processes for preparing industrially useful downstream derivatives of the nitrated compounds, as well as novel nitrated compounds and derivatives, and methods of using the derivatives in various applications.

4 Claims, No Drawings

(56) References Cited

U.S. PATENT DOCUMENTS

| | | | |
|---|---|---|---|
| 3,962,271 A | 6/1976 | Sidi et al. | |
| 4,304,942 A | 12/1981 | Ho | |
| 4,329,523 A | 5/1982 | James et al. | |
| 4,518,811 A | 5/1985 | Lhonore et al. | |
| 4,861,925 A | 8/1989 | Quirk | |
| 5,288,907 A | 2/1994 | Sherwin et al. | |
| 5,604,229 A * | 2/1997 | Fujita | C07C 215/10 514/252.1 |
| 6,072,063 A | 6/2000 | Eyrisch et al. | |
| 6,279,656 B1 | 8/2001 | Sinclair et al. | |
| 8,410,323 B2 | 4/2013 | Sawant et al. | |
| 8,431,754 B2 | 4/2013 | Sawant et al. | |
| 8,546,386 B2 * | 10/2013 | Green | A01N 33/08 514/231.8 |
| 8,558,039 B2 | 10/2013 | Sawant et al. | |
| 8,697,754 B2 * | 4/2014 | Brutto et al. | 514/667 |
| 2004/0152749 A1 | 8/2004 | Merianos et al. | |
| 2005/0054787 A1 | 3/2005 | Swedo et al. | |
| 2011/0028731 A1 | 2/2011 | Trauth et al. | |
| 2011/0092750 A1 | 4/2011 | Trauth et al. | |

OTHER PUBLICATIONS

Handlon et al., 1998, caplus an 1998:608613.*
Probert et al., 1995, caplus an 1995:621221.*
Hirose et al., Bioorganic&Medicinal Chemistry Letters, 1996, 6(22), 2647-2650.*
Yan et al. abstract, 2009, caplus an 2009:373576.*
Albright, "Nitration of Paraffins", Chemical Engineering, 1966, pp. 149-156.
Alkanolamines Kirk-Othmer Concise Encyclopedia of Chemical Technology, 1985, pp. 67-69.
Asinger et al., "Question of isomer formation during nitration of simple and substituted paraffinic hydrocarbons", Chem. Ber. 1967, vol. 100 No. 2, pp. 438-447.
Communication for EP Application 09733490.8, dated Jul. 28, 2014.
Communication received on EP Application 09733490.8, dated Jun. 26, 2015.
Dell'Erba et al., "Synthetic Exploitation of the Ring-Opening of 3,4-Dinitrothiophene. Part 3. Access to 1,4-Diaryl and 1,4-Dialkyl-2-nitrobutanes", Tetrahedron Letters, 1992, vol. 33 No. 46, pp. 7047-7048.
Examiner's Report issued on Canadian Application 2,720,646, dated May 7, 2015.
Final Office Action on U.S. Appl. No. 12/934,817, dated May 16, 2014.
Final Office Action on U.S. Appl. No. 12/934,817, dated Jul. 25, 2012.
First Office Action on Chinese Application 200980112776.X, dated Dec. 25, 2012.
Geiseler et al., "On the nitration of iso-octane with nitrogen dioxide", Z. Chem. 1962, vol. 2 No. 10, p. 311.
Geiseler, "Nitration of Saturated Hydrocarbons with Nitrogen Dioxide in the Liquid Phase", Angew. Chem., 1955, 9, p. 270-273.
International Search Report and Written Opinion on PCT/US2009/039901, dated Aug. 19, 2009.
Kornblum et al., "The Reaction of Silver Nitrite with Primary Alkyl Halides", Journal of the American Chemical Society, 1954, vol. 76, pp. 3209-3211.
Larock, "Comprehensive Organic Transformations: A Guide to Functional Group Preparations", VCH Publishers, 1989, pp. 411-415.
Nakahara et al., "Vapor-phase nitration of propane with nitric acid", Database Caplus, Chemical Abstracts Service, 1979.
Nishiwaki et al., "An Efficient Nitration of Light Alkanes and the Alkyl Side-Chain of Aromatic Compounds with Nitrogen Dioxide and Nitric Acid Catalyzed by N-Hydroxyphthalimide", Journal of Organic Chemistry, 2002, vol. 67 No. 16, pp. 5663-5668, 65663A American Chemical Society.
Nitro Alcohols, Kirk-Othmer Concise Encyclopedia of Chemical Technology, 1985, pp. 789-790.
Noland et al., "Heterocyclic Spiranes Oxazolidines from (1-Aminocyclohexyl)methanol", Journal of Organic Chemistry, 1960, vol. 25, pp. 1155-1159.
Non-Final Office Action on U.S. Appl. No. 12/934,817, dated Mar. 3, 2015.
Non-Final Office Action on U.S. Appl. No. 12/934,817, dated Mar. 8, 2012.
Notice of Allowance on U.S. Appl. No. 12/934,817, dated Jul. 16, 2015.
Notice of Reasons for Rejection issued on Japanese 2011-505090, dated Aug. 6, 2013.
Reexamination Notification issued on Chinese Application 200980112776.X, dated Apr. 7, 2015.
Rosini et al., "Functionalized Nitroalkanes as Useful Reagents for Alkyl Anion Synthons", Synthesis, 1988, pp. 833-847.
Ryer et al., "Reactions of N-Monoalkylhydroxylamines with Sulfur Dioxide, Sulfur Trioxide and Phthalic Anhydride", Journal of the American Chemical Society, 1951, vol. 73 No. 12, pp. 5675-5678.
Second Office Action on Chinese Application 200980112776.x, dated Aug. 15, 2013.
Stuhmer et al.,"N—N-Dialkylierte iso-Osy-beta-amino-alph.beta-diphenyl-athane", Chemische Berichte, vol. 83, pp. 66-68, Dec. 31, 1950.
Wheatley, "Alpha, alpha-Dimethylcholine: Esters and Carbamates", Journal of the American Chemical Society, 1954, vol. 76, pp. 2832-2835.
Woland et al., "Heterocyclic Spiranes Oxazolidines from (1-Aminocyclohexyl)methanol", J. Org. Chem. vol. 25, No. 7, pp. 1155-1159, Jul. 31, 1960.
Ghidini et al., "Synthesis of a new series of N-hydroxyl, N-alkylamides of aminoacids as ligands of NMDA glycine site," Eur. J. Med. Chem 34 (1999) pp. 711-717.
Search Report issued on European Application 16184250.5, dated Nov. 16, 2016.
Examination Report issued on Indian Appl. 6579/CHENP/2010, dated Feb. 9, 2017.

* cited by examiner

NITRATED HYDROCARBONS, DERIVATIVES, AND PROCESSES FOR THEIR MANUFACTURE

CROSS-REFERENCE TO RELATED APPLICATIONS

This application is a divisional of U.S. application Ser. No. 12/934,817, filed Sep. 27, 2010, which is a § 371 application of PCT International Patent Application Number PCT/US2009/039901 filed Apr. 8, 2009, which claims the benefit of U.S. Provisional Application No. 61/045,380 filed Apr. 16, 2008, each of which is incorporated herein by reference in its entirety.

FIELD OF THE INVENTION

The invention relates to a process for making nitrated hydrocarbons, such as nitroalkanes, nitrocycloalkanes, and nitroaralkyls, and to processes for making derivative compounds of the nitrated hydrocarbons. The invention also relates to new nitrated hydrocarbons and new derivatives.

BACKGROUND OF THE INVENTION

The nitration of hydrocarbons generally produces a variety of products depending upon the reaction conditions and the feedstock structure. Certain products, however, may be more desirable than others and it has been a long-time goal to selectively produce the more useful nitrated compounds at the expense of less useful compounds, such as oxidation byproducts.

In contrast to commercial vapor phase nitration, the mixed vapor-liquid phase or high pressure nitration of hydrocarbons has been postulated in the past to be a technique by which desirable nitroparaffins can be potentially produced. See e.g., U.S. Pat. No. 2,489,320 (Nygaard et al.) and Albright, L. F., "Nitration of Paraffins," Chem. Engr., (1966) pp. 149-156. The prior art mixed vapor-liquid phase process, however, was never practical for a number of reasons, including because the conversion of nitric acid is low, the nitric acid is not readily recoverable, problems with reactor corrosion by the nitric acid, and difficulty in controlling reaction exotherm.

Obtaining a high yield of nitrated hydrocarbons is a critical economic factor to be considered since low yields necessitate the use of more feed and therefore result in higher costs. Furthermore, when nitric acid is used as the nitrating agent, the unreacted nitric acid becomes a waste product and costs are incurred for proper disposal of the waste. High conversion of the reactant hydrocarbon is also economically critical in order to minimize capital and energy expenses associated with the purification and recycling of unreacted reactants. A need exists, therefore, for more economical, selective, and environmentally friendly processes for the manufacture of nitrated hydrocarbons and their derivatives.

BRIEF SUMMARY OF THE INVENTION

In one aspect, the invention provides a process for the nitration of hydrocarbons. The process comprises: providing a downflow configured reactor; reacting a hydrocarbon feedstock with aqueous nitric acid at a pressure of at least about 500 psi and a temperature of between about 140 and about 325 degrees Celsius; and recovering the formed nitrated compounds, wherein the aqueous nitric acid is a 10 to 50 weight percent solution.

In a second aspect, the invention provides processes for preparing industrially useful downstream derivatives of nitrated hydrocarbons, such as nitroalcohols, aminoalcohols, N-alkylaminoalcohols, alkylhydroxylamines, and oxazolidines.

In a third aspect, the invention provides nitrated hydrocarbons, and derivatives thereof.

The invention further provides methods of using the nitrated hydrocarbons and derivatives thereof in various applications.

DETAILED DESCRIPTION OF THE INVENTION

As noted above, in one aspect, the invention relates to a process for the nitration of hydrocarbons. The combination of reaction conditions, nitrating agent concentration, and use of a downflow reactor according to the invention provides the process with a number of improvements over the prior art, and particularly in terms of the reduced formation of oxidation byproducts and the increased conversion of starting materials to either desired product or to materials that are readily recyclable or treatable.

The invention process is carried out in a downflow configured reactor. That is, the reactor is positioned substantially vertically and the reactants are introduced at the upper end and the product mixture collected at the lower end of the reactor.

Operation of the reactor in a downflow mode according to the invention provides nitrated compounds that contain relatively low levels of oxidation byproducts as compared to prior art systems, which generally utilize horizontal, upflow, coiled or batch autoclave type apparatuses. Without wishing to be bound by any particular theory, it is believed that the advantages of the downflow reactor result primarily from its ability to minimize the amount and residence time of the liquid phase during the nitration reaction. The liquid phase in general contains a low mole ratio of hydrocarbons to nitric acid, which favors oxidation chemistry at the expense of nitration. Oxidation therefore primarily occurs in the liquid phase. Because the gas in a downflow reactor is the continuous phase and the liquid trickles down the reactor walls or packing, the amount of liquid phase(s) in the downflow reactor is maintained at a low level. Consequently oxidation chemistry is minimized.

In contrast, in an upflow reactor, also referred to as a bubble column, the liquid is the continuous phase (and bubbles rise quickly through the continuous liquid phase). Thus, an upflow reactor maximizes the liquid holdup. Because, as noted above, oxidation primarily occurs in the liquid phase, the upflow reactor maximizes the formation of oxidation byproducts. Similarly, coil and horizontal reactor configurations also increase liquid residence time and therefore oxidation chemistry as compared to a downflow reactor. A further disadvantage of coiled reactors is that they are not well-suited for industrial scale production because of the difficulty of fabricating large scale reactors in this shape.

The downflow configured reactor for use in the invention is preferably made of a corrosion resistant material, such as titanium. The reactor is optionally surrounded by a shell with input and output ports for circulating a heat transfer fluid. The heat transfer fluid, which can be, for example, an oil, allows the temperature of the reaction to be controlled to within the desired parameters. It should be noted, however, that because the reaction between the nitric acid and hydrocarbon is exothermic, use of a shell and a heat transfer fluid are not required. The temperature of the reaction can be regulated to be within the desired parameters by simply regulating the addition rate and/or concentration of the reactants.

To facilitate operation in downflow mode, the reactor is generally of an elongated and linear shape, such as a tube, and is positioned so that reactants are added through an entry port at or near the top of the reactor and then flowed down the reactor for sufficient residence time to allow reaction to occur and formation of the desired product. The product mixture is collected through an exit port at or near the bottom of the reactor.

The reactor is optionally packed in order to improve reactant mixing and heat transfer and/or to vary the reactor volume. Suitable packing materials include, for example, glass beads, random packing, or structured packing, such as those typically employed in distillation devices. Other packing materials are known in the art and may be used.

The hydrocarbon feed and nitric acid can be mixed, or partially mixed, prior to entry into the reactor or, alternatively, they can be added individually, with mixing to occur within the reactor. Further, the reactants, whether added together or individually, can be preheated prior to entry into the reactor.

The nitric acid is delivered to the reactor in the form of an aqueous solution that contains at least about 10 weight percent, preferably at least about 15 weight percent, more preferably at least about 20 weight percent, of the acid. Further, the solution contains no more than about 50 weight percent, preferably no more than about 40 weight percent, and more preferably no more than about 35 weight percent, of the acid. In further embodiments, the nitric acid solution contains between about 15 and about 40 weight percent of the acid. In other embodiments, the nitric acid solution contains between about 18 and about 35 weight of the acid.

The mole ratio of hydrocarbon to nitric acid should be at least about 1:1, more preferably at least about 1.2:1.

The reaction temperature within the reactor is generally controlled (for example with heat exchange fluid or using heat generated from the reaction, as described above) to at least about 140 degrees Celsius and to no more than about 325 degrees Celsius. In some embodiments, the temperature is at least about 180 degrees, at least about 200 degrees, at least about 230 degrees or at least about 240 degrees. In further embodiments, the temperature is no more than about 290 degrees, no more than about 280 degrees, no more than about 270 degrees, or no more than about 250 degrees. In other embodiments, the temperature is between about 200 and 250 degrees Celsius.

The pressure in the reactor is maintained at least about 500 psi, more preferably at least about 1000 psi (68 atm), and further preferably at least about 1200 psi (82 atm). Further preferably, the pressure is about 1600 psi (109 atm) or less, preferably about 1500 psi (102 atm) or less, more preferably about 1400 psi (95 atm) or less. In further embodiments, the pressure is between about 1000 psi (68 atm) and 1400 psi (95 atm). Various methods known in the art can be used for maintaining the pressure within the desired range including, for example, through the use of a back-pressure regulator.

The residence time of the reactants in the reactor is preferably at least about 30 seconds, more preferably at least about 90 seconds. Residence time can be controlled in various ways including, for example, by the length and/or width of the reactor or through the use of packing material. Residence time is determined by dividing the volume of the reactor by the inlet flow rates.

Following sufficient residence time, the nitration products are collected from the reactor through the reactor's exit port. Further processing, such as distillation, may be carried out on the nitrated products to, for example, isolate or purify the desirable materials.

Examples of reactant hydrocarbons which may be used in the process of the invention include, but are not limited to, alkanes and cycloalkanes (including alkyl substituted cycloalkanes), such as isobutane, n-butane, isopentane, n-pentane, n-hexane, n-heptane, n-octane, 2,3-dimethylbutane, cyclohexane, cyclopentane, and methylcyclohexane; aryl alkanes such as ethylbenzene, toluene, xylenes, isopropyl benzene; 1-methylnaphthalene and 2-methylnaphthalene and 4-methylbiphenyl; fused cycloalkanes, alkyl substituted fused aryl compounds, and fused cyclolalkane-aryl compounds (including alkyl substituted derivatives), such as tetralin, decalin, and methylnaphthalene. The nitration of reactants that already have one or more nitro substituents is also contemplated provided that the reactant still has an available hydrogen.

In one preferred embodiment of the first aspect of the invention, the hydrocarbon is a linear or branched alkane containing 4 or more carbon atoms, such as isobutane or n-butane, and the nitric acid is delivered as 25-35 weight percent, preferably about 30 weight percent, solution. For such hydrocarbon materials, it is preferred to use a reaction temperature of between about 170 and 325 degrees Celsius and a pressure between about 800 and 1600 psi. For isobutane, a temperature of at least about 200 degrees and a pressure of about 1000 to 1400 psi are particularly favorable. For n-butane, a temperature of at least about 220 degrees and a pressure of about 1000 to 1500 psi are favorable.

In another preferred embodiment, the hydrocarbon is a cyclic alkane, such as cyclohexane. The nitric acid is preferably delivered as 25-35 weight percent, more preferably about 30 weight percent, solution. For such hydrocarbons, the preferred reaction temperature is at least 200 degrees Celsius and the preferred pressure is between about 600 and 1200 psi.

In a further preferred embodiment, the hydrocarbon is an arylalkane, such as toluene, and the nitric acid is delivered as 25-35 weight percent, more preferably about 30 weight percent, solution. The preferred reaction temperature for nitration of toluene is at least 180 degrees and the preferred pressure is between about 900 and 1200 psi.

As noted above, one of the advantages of the process of invention is that it results in increased conversion rates of starting reactants to either desired product or to materials that are readily recyclable or treatable, as compared to prior art systems. In some embodiments, therefore, at least 90 weight %, more preferably at least 95 weight %, of the nitric acid is consumed during the nitration reaction (determined as follows: (grams nitric acid in−grams nitric acid out)/grams nitric acid in). Most of the converted nitric acid that does not result in nitrated hydrocarbons is, for some feedstocks, in the readily recovered form of nitric oxide (NO).

In a further preferred embodiment, the conversion of hydrocarbon feedstock to nitrated hydrocarbon (determined by dividing the number of moles of nitrated hydrocarbon formed by the number of moles of hydrocarbon that is fed into the reaction) is at least 25 mole percent, more preferably at least 40 mole percent, and even more preferably at least 50 mole percent.

Preferred nitrated hydrocarbons prepared according to the process of the invention include compounds of the formula (I):

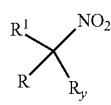

wherein R is $C_2$-$C_{20}$ alkyl, $C_3$-$C_{12}$ cycloalkyl, cycloalkyl-alkyl-, aryl, or aryl-alkyl-; and $R^1$ is H or $C_1$-$C_{12}$ alkyl; or R and $R^1$ together with the carbon to which they are attached form a $C_3$-$C_{12}$ cycloalkyl ring; and $R_y$ is H or $C_1$-$C_6$ alkyl, provided that when R is an ethyl group, $R^1$ and $R_y$ are not simultaneously H. More preferred are compounds of formula (I) wherein R is $C_2$-$C_8$ alkyl or $C_3$-$C_8$ cycloalkyl. Also preferred are compounds in which one of $R^1$ and $R_y$ is an alkyl group.

It should be noted that some of the nitrated compounds and derivatives described herein are formed as mixtures. For example, the nitration of n-hexane forms 1, 2 and 3-nitrohexanes concurrently. While it may be desirable to obtain one or more of the isomers in a substantially pure form, in many applications isomer purity is not necessary and the combined mixture is generally suitable for use as is. The invention therefore encompasses mixtures of two or more of the nitrated compounds, and mixtures of two or more of their derivatives.

In a second aspect, the invention provides processes for the preparation of a variety of downstream derivatives (or mixtures thereof) from the nitrated hydrocarbons described above, and preferably from the compounds of formula (I) (see Scheme 1). Such derivatives are useful in many industrially important applications.

$CH(OH)$—$R^5$, provided that when R is an ethyl group, $R^2$ is not H; or R and $R^2$ together with the carbon to which they are attached form a $C_3$-$C_{12}$ cycloalkyl ring; and $R^5$ is independently H, $C_1$-$C_{12}$ alkyl, $C_3$-$C_{12}$ cycloalkyl, or aryl. The process of this embodiment comprises: (a) providing a nitrated hydrocarbon of formula (I), wherein $R_y$ is H, prepared as described above; and (b) condensing the nitrated hydrocarbon with an aldehyde in the presence of an alkaline catalyst.

A variety of alkaline catalysts can be used for the condensation reaction, although sodium hydroxide or trimethylamine are preferred. Aldehydes for the condensation step are generally of the formula $R^5$—C(=O)—H and include, for instance, such aldehydes as formaldehyde, acetaldehyde, propionaldehyde, butyraldehyde, valeraldehyde, cyclohexanecarbaldehyde, and benzaldehyde (optionally substituted with alkyl, nitro, alkoxy, hydroxy, halogen, amide or ester groups), with formaldehyde being particularly preferred. Typically the reaction involves batchwise or continuously reacting the nitrated compound with an aqueous solution of the aldehyde at a mole ratio of about 1:1 and at a temperature of approximately 70-80° C. The catalyst is preferably used in an amount sufficient to provide a normality of about 0.01-0.05 in the reaction mixture. Typically, the reaction is conducted without solvent. The product can be used directly as the aqueous solution or it can be recovered such as by stripping off volatiles under vacuum. Various known techniques, such as crystallization, may be used for further purifying the product.

For nitroalkanes of formula (I) in which the nitro group is present on a carbon bearing two hydrogens (i.e., $R^1$ and $R_y$ are both H), the condensation may optionally occur up to two times to generate a nitroalcohol with two hydroxy

SCHEME 1

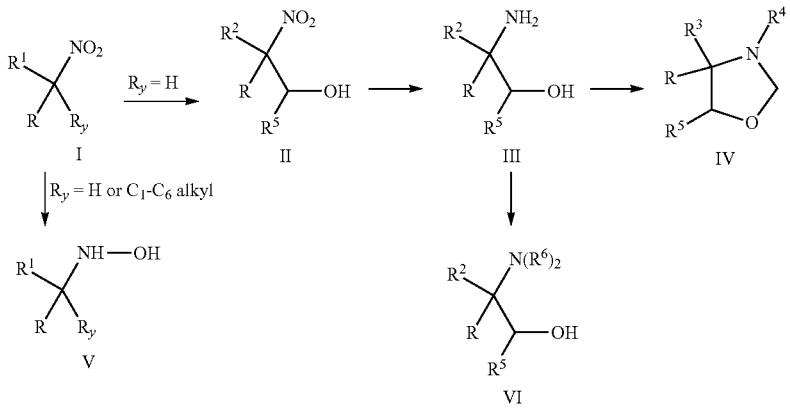

Thus, according to one embodiment of the second aspect of the invention, a process is provided for the preparation of a nitroalcohol of the formula II:

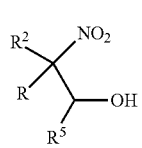

wherein R is $C_2$-$C_{20}$ alkyl, $C_3$-$C_{12}$ cycloalkyl, cycloalkyl-alkyl-, aryl, or aryl-alkyl-; $R^2$ is H, $C_1$-$C_{12}$ alkyl, or groups (i.e., $R^2$ in formula (II) is —$CH(R^5)OH$) by using two or more equivalents of the aldehyde.

In some embodiments, preferred compounds of formula (II) prepared according to the above process are those wherein R is $C_2$-$C_8$ alkyl, more preferably $C_2$-$C_6$ alkyl. Also preferably, $R^2$ is $C_1$-$C_3$ alkyl. Further preferably, $R^5$ is H.

In other embodiments, preferred compounds of formula (II) are those wherein R and $R^2$ together with the carbon to which they are attached form a $C_3$-$C_8$ cycloalkyl ring, more preferably a cyclohexyl ring.

Particularly preferred compounds of formula (II) are: 2-methyl-2-nitro-1-octanol; 2-ethyl-2-nitro-1-heptanol;

2-nitro-2-propyl-1-hexanol; 2-methyl-2-nitro-1-hexanol; 2-ethyl-2-nitro-1-pentanol; and 1-hydroxymethyl-1-nitrocyclohexane.

In a second embodiment of the second aspect of the invention, a process is provided for the preparation of an aminoalcohol of the formula (III):

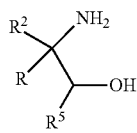

III wherein R is $C_2$-$C_{20}$ alkyl, $C_3$-$C_{12}$ cycloalkyl, cycloalkylalkyl-, aryl, or aryl-alkyl-; $R^2$ is H, $C_1$-$C_{12}$ alkyl, or CH(OH)—$R^5$, provided that when R is an ethyl group, $R^2$ is not H; or R and $R^2$ together with the carbon to which they are attached form a $C_3$-$C_{12}$ cycloalkyl ring; and $R^5$ is independently H, $C_1$-$C_{12}$ alkyl, $C_3$-$C_{12}$ cycloalkyl, or aryl. The process of this embodiment comprises: (a) providing a nitroalcohol of formula (II) prepared as described above; and (b) chemically reducing the nitroalcohol to the aminoalcohol. Chemical reduction of nitro compounds to amine is well known and a variety of techniques may be found in "Comprehensive Chemical Transformations", Richard C. Larock ed.; VCH Publishers, 1989, pages 411-415. Hydrogenation in the presence of a hydrogenation catalyst is preferred.

Hydrogenation with a hydrogenation catalyst is a well known technique and the conditions for the reaction can be easily determined by a person of ordinary skill in the art. Suitable catalysts include, without limitation, Raney nickel, platinum and palladium. Raney nickel is preferred. Typically, the hydrogenation is conducted in an aqueous methanol or ethanol solution at a temperature of about 70-100° C. and a pressure of about 400-600 p.s.i.g. The catalyst is used in a concentration of between about 2 and 10 weight percent of the nitroalcohol to be hydrogenated. The product can be readily recovered through filtration of catalyst, followed by stripping of solvents. Various known techniques, such as crystallization or distillation, may be used for further purifying the product.

The aminoalcohols of formula (III) are useful, for instance, as neutralizing agents and pigment dispersants such as in paints and coatings, as $CO_2$ or $H_2S$ scavengers in petroleum refinery operations and natural gas processing, and as catalysts or hardeners in epoxy or polyurethane applications. In some embodiments, preferred compounds of formula (III) are those wherein R is $C_2$-$C_8$ alkyl, more preferably $C_2$-$C_6$ alkyl. Also preferably, $R^2$ is $C_1$-$C_3$ alkyl. Further preferably, $R^5$ is H. In some embodiments, it is preferred that $R^5$ is phenyl, optionally substituted with hydroxy, halogen, nitro, $C_1$-$C_6$ alkoxy, —$CO_2$—$C_1$-$C_6$ alkyl, or —$CONR_AR_B$, where $R_A$ and $R_B$ are independently H or $C_1$-$C_6$ alkyl.

In other embodiments, preferred compounds of formula (III) are those wherein R and $R^2$ together with the carbon to which they are attached form a $C_3$-$C_8$ cycloalkyl ring, more preferably a cyclohexyl ring.

Particularly preferred compounds of formula (III) are: 2-amino-2-methyl-1-octanol; 2-amino-2-ethyl-1-heptanol; 2-amino-2-propyl-1-hexanol; 2-amino-2-methyl-1-hexanol; 2-amino-2-ethyl-1-pentanol; and 1-amino-1-hydroxymethylcyclohexane.

According to a third embodiment, a process is provided for the preparation of an oxazolidine of the formula (IV):

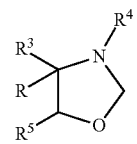

IV wherein R is $C_2$-$C_{20}$ alkyl, $C_3$-$C_{12}$ cycloalkyl, cycloalkylalkyl-, aryl, or aryl-alkyl-; $R^3$ is H or $C_1$-$C_{12}$ alkyl, provided that when R is an ethyl group, $R^3$ is not H; or R and $R^3$ together with the carbon to which they are attached form a $C_3$-$C_{12}$ cycloalkyl ring; and $R^4$ is H; or $R^3$, $R^4$, and the atoms to which they are attached form an oxazolidine ring that is optionally substituted with $C_1$-$C_6$ alkyl; and $R^5$ is H, $C_1$-$C_{12}$ alkyl, $C_3$-$C_{12}$ cycloalkyl, or aryl. The process of this embodiment comprises: (a) providing an aminoalcohol of formula (III) prepared as described above; and (b) reacting the aminoalcohol of formula (III) with formaldehyde.

Single oxazolidine structures of formula (IV) may be produced by the reaction of equimolar amounts of formaldehyde and the aminoalcohol of formula (III). Bis-oxazolidines can be prepared by using 2 or greater equivalents of formaldehyde with a compound of formula (III) in which $R^2$ is CH(OH)—$R^5$.

Typically, the reaction is conducted without solvent at about 50-70° C. temperature for a period of 1-2 hours. The product can be directly used without additional processing as the aqueous solution obtained from the condensation reaction, or further purification can be carried out, such as by distillation and/or crystallization.

Oxazolidines of formula (IV) are useful in a variety of applications, including as curing agents, such as for phenolic novolac resins, or as biocides. In some embodiments, preferred compounds of formula (IV) prepared according to the above process are those wherein R is $C_2$-$C_{12}$ alkyl, more preferably $C_2$-$C_{10}$ alkyl. Also preferably, $R^3$ is H or $C_1$-$C_8$ alkyl. Further preferably, $R^5$ is H.

In other embodiments, preferred compounds of formula (IV) are those wherein $R_3$ and $R_4$, together with the carbon to which they are attached, form an oxazolidine ring.

According to a fourth embodiment of the second aspect of the invention, a process is provided for the preparation of an N-alkylhydroxylamine of the formula V:

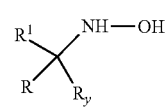

V wherein R is $C_2$-$C_{20}$ alkyl, $C_3$-$C_{12}$ cycloalkyl, cycloalkylalkyl-, aryl, or aryl-alkyl-; and $R^1$ is H, or $C_1$-$C_{12}$ alkyl; or R and $R^1$ together with the carbon to which they are attached form a $C_3$-$C_{12}$ cycloalkyl ring; and $R_y$ is H or $C_1$-$C_6$ alkyl, provided that when R is an ethyl group, $R^1$ and $R_y$ are not simultaneously H. The process of this embodiment comprises: (a) providing a nitrated hydrocarbon of formula (I) prepared as described above; (b) chemically reducing the nitrated hydrocarbon to the hydroxylamine. Chemical reductions of nitro compounds to hydroxylamines are well known and a variety of techniques may be used. Examples of chemical reducing agents used to prepare hydroxylamines from nitroalkanes include samarium iodide, Zn/NH4Cl, aluminum amalgam, and lithium aluminum hydride.

Partially hydrogenating the nitrated hydrocarbon in the presence of a hydrogenation catalyst is a preferred technique.

Partial hydrogenation of a nitro groups to hydroxylamines is well known in the art and described, for instance, in U.S. Pat. No. 5,288,907 which is incorporated herein by reference. A preferred catalyst for the partial hydrogenation is $Pd/Al_2O_3$, although other well known catalysts may be used. Typically the hydrogenation is conducted in water or methanol at 50-75° C. and 30-600 p.s.i.g. $H_2$, with good agitation for 4-6 hours. The product can be recovered by filtering off the catalyst, then storing, and using directly as an aqueous solution, or further isolation can done, such as by recrystallization.

Compounds of formula (V) function as radical scavengers and are therefore useful in a variety of applications, such as stabilizers and/or corrosion control agents in fuel, stabilizers of monomers, or as short-stopping agents in rubber polymerizations. In some embodiments, preferred compounds of formula (V) are those wherein and R is $C_2$-$C_8$ alkyl and $R^1$ is $C_1$-$C_6$ alkyl. Also preferred are compounds wherein R and $R^1$ together with the carbon to which they are attached form a $C_3$-$C_{12}$ cycloalkyl ring, more preferably a $C_5$-$C_{10}$ ring. Particularly preferred compounds of formula (V) are N-tert-butylhydroxylamine, N-sec-butylhydroxylamine, N-cyclohexylhydroxylamine, mixtures of n-N-hexylhydroxylamines, mixtures of n-N-octylhydroxylamines.

The nitrated hydrocarbons and derivatives thereof can be further derivatized to provide additional useful materials. By way of one non-limiting example, the aminoalcohol of formula (III) can be mono or bis-alkylated at the amine to yield N-alkylated aminoalcohols of formula VI:

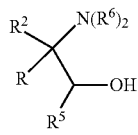

VI wherein R is $C_2$-$C_{20}$ alkyl, $C_3$-$C_{12}$ cycloalkyl, cycloalkyl-alkyl-, aryl, or aryl-alkyl-; $R^2$ is H, $C_1$-$C_{12}$ alkyl, or CH(OH)—$R^5$, provided that when R is an ethyl group, $R^2$ is not H; or R and $R^2$ together with the carbon to which they are attached form a $C_3$-$C_{12}$ cycloalkyl ring; $R^5$ is independently H, $C_1$-$C_{12}$ alkyl, $C_3$-$C_{12}$ cycloalkyl, or aryl; and $R^6$ is independently H or $C_1$-$C_6$ alkyl. Compounds of formula VI find use, for instance, as neutralizing agents, dispersants and polyurethane catalysts. A preferred alkylated compound according to this example is 1-hydroxymethyl-1-(N,N-dimethylamino)cyclohexane.

The compound of formula VI is prepared by reductive alkylation (e.g., methylation) using 1 or 2 equivalents of an aldehyde as the alkyl source (e.g., formaldehyde for methylation) and hydrogen over a hydrogenation catalyst, such as Raney nickel, at elevated temperature (e.g., 70-130° C.) and pressure (e.g., 600-750 psi).

In its third aspect, the invention provides novel nitrated hydrocarbons and novel derivative compounds. According to a first embodiment of this third aspect, the nitrated hydrocarbons are of the formula I-1:

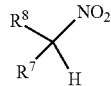

I-1 wherein $R^7$ is linear $C_2$-$C_{17}$ alkyl; and $R^8$ is H or linear $C_1$-$C_8$ alkyl, provided that $R^7$ and $R^8$ together with the carbon to which they are attached form a linear $C_{10}$-$C_{18}$ alkyl chain, and provided that the compound is not: 1-nitrodecane, 2-nitrodecane, 1-nitroundecane, 2-nitroundecane, 3-nitroundecane, 4-nitroundecane, 5-nitroundecane, 6-nitroundecane, 1-nitrododecane, 2-nitrododecane, 3-nitrododecane, 4-nitrododecane, 5-nitrododecane, 6-nitrododecane, 1-nitrotridecane, 2-nitrotridecane, 3-nitrotridecane, 6-nitrotridecane, 1-nitrotetradecane, 1-nitropentadecane, 1-nitrohexadecane, 2-nitrohexadecane, 1-nitroheptadecane, 1-nitrooctadecane, or 2-nitrooctadecane.

Preferred compounds according to formula I-1 include those wherein $R^7$ and $R^8$ together with the carbon to which they are attached form a linear $C_{12}$-$C_{18}$ alkyl, $C_{14}$-$C_{18}$ alkyl, $C_{16}$-$C_{18}$ alkyl, $C_{10}$-$C_{16}$ alkyl, $C_{10}$-$C_{14}$ alkyl, or $C_{10}$-$C_{12}$ alkyl.

Also preferred are compounds wherein $R^7$ and $R^8$ are unsubstituted.

Particularly preferred compounds according to formula I-1 are: 3-nitrodecane, 4-nitrodecane, 5-nitrodecane, 4-nitrotridecane, 5-nitrotridecane, 7-nitrotridecane, 2-nitrotetradecane, 3-nitrotetradecane, 4-nitrotetradecane, 5-nitrotetradecane, 6-nitrotetradecane, 7-nitrotetradecane, 2-nitropentadecane, 3-nitropentadecane, 4-nitropentadecane, 5-nitropentadecane, 6-nitropentadecane, 7-nitropentadecane, 8-nitropentadecane, 3-nitrohexadecane, 4-nitrohexadecane, 5-nitrohexadecane, 6-nitrohexadecane, 7-nitrohexadecane, 8-nitrohexadecane, 2-nitroheptadecane, 3-nitroheptadecane, 4-nitroheptadecane, 5-nitroheptadecane, 6-nitroheptadecane, 7-nitroheptadecane, 8-nitroheptadecane, 9-nitroheptadecane, 3-nitrooctadecane, 4-nitrooctadecane, 5-nitrooctadecane, 6-nitrooctadecane, 7-nitrooctadecane, 8-nitrooctadecane, and 9-nitrooctadecane.

In a second embodiment of its third aspect, the invention provides a nitroalcohol of the formula II-1:

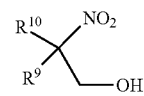

II-1 wherein $R^9$ is linear $C_2$-$C_{17}$ alkyl; and $R^{10}$ is H, linear $C_1$-$C_8$ alkyl, or $CH_2OH$; or $R^9$, $R^{10}$, and the carbon to which they are attached form an eight membered cycloalkyl ring; provided that:

when $R^{10}$ is H or linear $C_1$-$C_8$ alkyl, $R^9$ and $R^{10}$, together with the carbon to which they are attached, form a linear $C_5$-$C_{18}$ alkyl chain, when $R^{10}$ is $CH_2OH$, $R^9$ is linear $C_{12}$-$C_{16}$ alkyl; and the compound is not: 2-nitro-1-hexanol, 2-nitro-1-heptanol, 2-nitro-1-octanol, 2-methyl-2-nitro-1-heptanol, or 2-nitro-1-dodecanol.

Preferred compounds according to formula II-1 include those wherein when $R^{10}$ is H or linear $C_1$-$C_8$ alkyl, $R^9$ and $R^{10}$, together with the carbon to which they are attached, form a linear $C_7$-$C_{18}$ alkyl, $C_9$-$C_{18}$ alkyl, $C_{11}$-$C_{18}$ alkyl, $C_{13}$-$C_{18}$ alkyl, $C_{15}$-$C_{18}$ alkyl, $C_5$-$C_{16}$ alkyl, $C_5$-$C_{14}$ alkyl, $C_5$-$C_{12}$ alkyl, $C_5$-$C_{10}$ alkyl, or $C_5$-$C_8$ alkyl chain.

Further preferred are compounds wherein when $R^{10}$ is $CH_2OH$, $R^9$ is linear $C_{14}$-$C_{16}$ alkyl, or $C_{12}$-$C_{13}$ alkyl.

Also preferred are compounds wherein $R^9$ and $R^{10}$ are unsubstituted.

Particularly preferred compounds according to formula II-1 are: 2-methyl-2-nitro-1-pentanol, 2-ethyl-2-nitro-1-butanol, 2-methyl-2-nitro-1-hexanol, 2-ethyl-2-nitro-1-pentanol, 2-ethyl-2-nitro-1-hexanol, 2-nitro-2-propyl-1-pentanol, 2-nitro-1-nonanol, 2-methyl-2-nitro-1-octanol, 2-ethyl-2-nitro-1-heptanol, 2-nitro-2-propyl-1-hexanol, 2-nitro-1-decanol, 2-methyl-2-nitro-1-nonanol, 2-ethyl-2-nitro-1-octanol, 2-nitro-2-propyl-1-heptanol, 2-butyl-2-nitro-1-hexanol, 2-nitro-1-undecanol, 2-methyl-2-nitro-1-decanol, 2-ethyl-2-nitro-1-nonanol, 2-propyl-2-nitro-1-octanol, 2-butyl-2-nitro-1-heptanol, 2-methyl-2-nitro-1-undecanol, 2-ethyl-2-nitro-1-decanol, 2-propyl-2-nitro-1-nonanol, 2-butyl-2-nitro-1-octanol, 2-pentyl-2-nitro-1-heptanol, 2-nitro-1-tridecanol, 2-methyl-2-nitro-1-dodecanol, 2-ethyl-2-nitro-1-undecanol, 2-propyl-2-nitro-1-decanol, 2-butyl-2-nitro-1-nonanol, 2-pentyl-2-nitro-1-octanol, 2-nitro-1-tetradecanol, 2-hydroxymethyl-2-nitro-1-tetradecanol, 2-methyl-2-nitro-1-tridecanol, 2-ethyl-2-nitro-1-dodecanol, 2-propyl-2-nitro-1-undecanol, 2-butyl-2-nitro-1-decanol, 2-pentyl-2-nitro-1-nonanol, 2-hexyl-2-nitro-1-octanol, 2-nitro-1-pentadecanol, 2-hydroxymethyl-2-nitro-1-pentadecanol, 2-methyl-2-nitro-1-tetradecanol, 2-ethyl-2-nitro-1-tridecanol, 2-propyl-2-nitro-1-dodecanol, 2-butyl-2-nitro-1-undecanol, 2-pentyl-2-nitro-1-decanol, 2-hexyl-2-nitro-1-nonanol, 2-heptyl-2-nitro-1-octanol, 2-nitro-1-hexadecanol, 2-hydroxymethyl-2-nitro-1-hexadecanol, 2-methyl-2-nitro-1-pentadecanol, 2-ethyl-2-nitro-1-tetradecanol, 2-propyl-2-nitro-1-tridecanol, 2-butyl-2-nitro-1-dodecanol, 2-pentyl-2-nitro-1-undecanol, 2-hexyl-2-nitro-1-decanol, 2-heptyl-2-nitro-1-nonanol, 2-nitro-1-heptadecanol, 2-hydroxymethyl-2-nitro-1-heptadecanol, 2-methyl-2-nitro-1-hexadecanol, 2-ethyl-2-nitro-1-pentadecanol, 2-propyl-2-nitro-1-tetradecanol, 2-butyl-2-nitro-1-tridecanol, 2-pentyl-2-nitro-dodecanol, 2-hexyl-2-nitro-1-undecanol, 2-heptyl-2-nitro-1-decanol, 2-nitro-1-octadecanol, 2-hydroxymethyl-2-nitro-1-octadecanol, 2-methyl-2-nitro-1-heptadecanol, 2-ethyl-2-nitro-1-hexadecanol, 2-propyl-2-nitro-1-pentadecanol, 2-butyl-2-nitro-1-tetradecanol, 2-pentyl-2-nitro-1-tridecanol, 2-hexyl-2-nitro-1-dodecanol, 2-heptyl-2-nitro-1-undecanol, 2-octyl-2-nitro-1-decanol, 2-nitro-1-nonadecanol, 2-methyl-2-nitro-1-octadecanol, 2-ethyl-2-nitro-1-heptadecanol, 2-propyl-2-nitro-1-hexadecanol, 2-butyl-2-nitro-1-pentadecanol, 2-pentyl-2-nitro-1-tetradecanol, 2-hexyl-2-nitro-1-tridecanol, 2-heptyl-2-nitro-1-dodecanol, 2-octyl-2-nitro-1-undecanol, and 1-hydroxymethyl-1-nitrocyclooctane.

It should be noted that that the nitration process described above is the preferred procedure by which most of the compounds of formula I-1 are prepared. However, the process tends to provide low yields of 1-nitroalkane products. Therefore, for preparing 1-nitroalkane products, other higher yielding procedures are preferred. One such suitable procedure well known in the art is described in Kornblum, et al., J. Am. Chem. Soc., Vol. 76, pp 3209-3211, 1954. By way of illustration, a typical procedure for the preparation of 1-nitrooctane is provided in the examples below.

In a third embodiment, the invention provides aminoalcohols of the formula III-1:

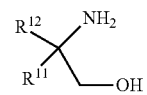

wherein $R^{11}$ is linear $C_2$-$C_{17}$ alkyl; and $R^{12}$ is H, linear $C_1$-$C_8$ alkyl, or $CH_2OH$; or $R^{11}$, $R^{12}$, and the carbon to which they are attached form a $C_9$-$C_{11}$ cycloalkyl ring; provided that:

when $R^{12}$ is H or linear $C_1$-$C_8$ alkyl, $R^{11}$ and $R^{12}$, together with the carbon to which they are attached, form a linear $C_6$-$C_{18}$ alkyl chain;

when $R^{12}$ is $CH_2OH$, $R^{11}$ is linear $C_7$-$C_{17}$ alkyl; and the compound is not: 2-amino-1-heptanol, 2-amino-2-methyl-1-hexanol, 2-amino-1-octanol, 2-amino-2-ethyl-1-hexanol, 2-amino-1-nonanol, 2-amino-2-methyl-1-octanol, 2-amino-1-decanol, 2-amino-2-octyl-1,3-propanediol, 2-amino-2-butyl-1-hexanol, 2-amino-1-undecanol, 2-amino-1-dodecanol, 2-amino-2-decyl-1,3-propanediol, 2-amino-1-tridecanol, 2-amino-2-methyl-1-dodecanol, 2-amino-1-tetradecanol, 2-amino-2-dodecyl-1,3-propanediol, 2-amino-2-methyl-1-tridecanol, 2-amino-1-pentadecanol, 2-amino-2-tridecyl-1,3-propanediol, 2-amino-1-hexadecanol, 2-amino-2-tetradecyl-1,3-propanediol, 2-amino-2-methyl-1-pentadecanol, 2-amino-2-hexyl-1-decanol, 2-amino-1-heptadecanol, 2-amino-2-pentadecyl-1,3-propanediol, 2-amino-1-octadecanol, or 2-amino-2-hexadecyl-1,3-propanediol.

Preferred compounds according to formula III-1 include those wherein, when $R^{12}$ is H or linear $C_1$-$C_8$ alkyl, $R^{11}$ and $R^{12}$ together with the carbon to which they are attached form a linear $C_8$-$C_{18}$ alkyl, $C_{10}$-$C_{18}$ alkyl, $C_{12}$-$C_{18}$ alkyl, $C_{14}$-$C_{18}$ alkyl, $C_{16}$-$C_{18}$ alkyl, $C_6$-$C_{16}$ alkyl, $C_6$-$C_{14}$ alkyl, $C_6$-$C_{12}$ alkyl, $C_6$-$C_{10}$ alkyl, or $C_6$-$C_8$ alkyl chain.

Further preferred are compounds wherein, when $R^{12}$ is $CH_2OH$, $R^{11}$ is linear $C_7$-$C_{15}$ alkyl, $C_7$-$C_{13}$ alkyl, $C_7$-$C_{11}$ alkyl, $C_7$-$C_9$ alkyl, $C_9$-$C_{17}$ alkyl, $C_{11}$-$C_{17}$ alkyl, $C_{13}$-$C_{17}$ alkyl, or $C_{15}$-$C_{17}$ alkyl.

Also preferred are compounds wherein $R^{11}$ and $R^{12}$ are unsubstituted.

Particularly preferred compounds according to formula III-1 are: 2-amino-2-ethyl-1-pentanol, 2-amino-2-methyl-1-heptanol, 2-amino-2-propyl-1-pentanol, 2-amino-2-heptyl-1,3-propanediol, 2-amino-2-ethyl-1-heptanol, 2-amino-2-propyl-1-hexanol, 2-amino-2-methyl-1-nonanol, 2-amino-2-ethyl-1-octanol, 2-amino-2-propyl-1-heptanol, 2-amino-2-nonyl-1,3-propanediol, 2-amino-2-methyl-1-decanol, 2-amino-2-ethyl-1-nonanol, 2-amino-2-propyl-1-octanol, 2-amino-2-butyl-1-heptanol, 2-amino-2-methyl-1-undecanol, 2-amino-2-ethyl-1-decanol, 2-amino-2-propyl-1-nonanol, 2-amino-2-butyl-1-octanol, 2-amino-2-pentyl-1-heptanol, 2-amino-2-undecyl-1,3-propanediol, 2-amino-2-ethyl-1-undecanol, 2-amino-2-propyl-1-decanol, 2-amino-2-butyl-1-nonanol, 2-amino-2-pentyl-1-octanol, 2-amino-2-ethyl-1-dodecanol, 2-amino-2-propyl-1-undecanol, 2-amino-2-butyl-1-decanol, 2-amino-2-pentyl-1-nonanol, 2-amino-2-hexyl-1-octanol, 2-amino-2-methyl-1-tetradecanol, 2-amino-2-ethyl-1-tridecanol, 2-amino-2-propyl-1-dodecanol, 2-amino-2-butyl-1-undecanol, 2-amino-2-pentyl-1-decanol, 2-amino-2-hexyl-1-nonanol, 2-amino-2-ethyl-1-tetradecanol, 2-amino-2-propyl-1-tridecanol, 2-amino-2-butyl-1-dodecanol, 2-amino-2-pentyl-1-undecanol, 2-amino-2-heptyl-1-nonanol, 2-amino-2-methyl-1-hexadecanol, 2-amino-2-ethyl-1-pentadecanol, 2-amino-2-propyl-1-tetradecanol, 2-amino-2-butyl-1-tridecanol, 2-amino-2- pentyl-1-dodecanol, 2-amino-2-hexyl-1-undecanol, 2-amino-2-heptyl-1-decanol, 2-amino-2-methyl-1-heptadecanol, 2-amino-2-ethyl-1-hexadecanol, 2-amino-2-propyl-1-pentadecanol, 2-amino-2-butyl-1-tetradecanol, 2-amino-2-pentyl-1-tridecanol, 2-amino-2-hexyl-1-dodecanol, 2-amino-2-heptyl-1-undecanol, 2-amino-2-octyl-1-decanol, 2-amino-1-nonadecanol, 2-amino-2-heptadecyl-1,3-propanediol, 2-amino-2-methyl-1-octadecanol, 2-amino-2-ethyl-1-heptadecanol, 2-amino-2-propyl-1-hexadecanol, 2-amino-2-butyl-1-pentadecanol, 2-amino-2-pentyl-1-tetradecanol, 2-amino-2-hexyl-1-tridecanol, 2-amino-2-heptyl-1-dodecanol, 2-amino-2-octyl-1-undecanol, 1-hydroxymethyl-1-aminocyclononane, 1-hydroxymethyl-1-aminocyclodecane, and 1-hydroxymethyl-1-aminocycloundecane.

In a fourth embodiment of its third aspect, the invention provides oxazolidines of the formula IV-1:

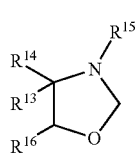

wherein $R^{13}$ is $C_2$-$C_{20}$ alkyl, $C_3$-$C_{12}$ cycloalkyl, aryl, or aryl-alkyl-; $R^{14}$ is H or $C_1$-$C_{12}$ alkyl, provided that when $R^{13}$ is an ethyl group, $R^{14}$ is not H; or $R^{13}$ and $R^{14}$ together with the carbon to which they are attached form a $C_3$-$C_{12}$ cycloalkyl ring; $R^{15}$ is H; or $R^{14}$, $R^{15}$, and the atoms to which they are attached form an oxazolidine ring that is optionally substituted with $C_1$-$C_6$ alkyl; and $R^{16}$ is H, $C_1$-$C_{12}$ alkyl, $C_3$-$C_{12}$ cycloalkyl, or aryl, provided that the compound is not: 5-propyl-1-aza-3,7-dioxabicyclo[3.3.0]octane, 4,4-diethyl-1-oxa-3-azacyclopentane, 3-oxa-1-azaspiro[4.4]nonane, 3-oxa-1-azaspiro[4.5]decane, or 3-oxa-1-azaspiro[4.7]dodecane.

Preferred compounds according to formula IV-I include those wherein $R^{13}$ is $C_2$-$C_{20}$ alkyl. Also preferred are those wherein $R^{13}$ is linear $C_4$-$C_{20}$ alkyl, $C_4$-$C_{20}$ alkyl, $C_6$-$C_{20}$ alkyl, $C_{12}$-$C_{20}$ alkyl, $C_{14}$-$C_{20}$ alkyl, $C_{16}$-$C_{20}$ alkyl, $C_{18}$-$C_{20}$ alkyl, $C_2$-$C_{18}$ alkyl, $C_2$-$C_{16}$ alkyl, $C_2$-$C_{14}$ alkyl, $C_2$-$C_{12}$ alkyl, $C_2$-$C_{10}$ alkyl, $C_2$-$C_8$ alkyl, $C_2$-$C_6$ alkyl, or $C_2$-$C_4$ alkyl.

Preferred compounds of formula IV-I also include those wherein $R^{14}$ is H. Further preferred are those wherein $R^{14}$ is linear $C_1$-$C_{12}$ alkyl, $C_3$-$C_{12}$ alkyl, $C_5$-$C_{12}$ alkyl, $C_7$-$C_{12}$ alkyl, $C_9$-$C_{12}$ alkyl, $C_1$-$C_{10}$ alkyl, $C_1$-$C_8$ alkyl, $C_1$-$C_6$ alkyl, $C_1$-$C_4$ alkyl, or $C_1$-$C_2$ alkyl.

Also preferred are compounds wherein $R^{16}$ is H.

Particularly preferred compounds of formula IV-I are: 4-propyl-1-oxa-3-azacyclopentane, 4-ethyl-4-methyl-1-oxa-3-azacyclopentane, 4-butyl-1-oxa-3-azacyclopentane, 5-butyl-1-aza-3,7-dioxabicyclo[3.3.0]octane, 4-propyl-4-methyl-1-oxa-3-azacyclopentane, 4-pentyl-1-oxa-3-azacyclopentane, 5-pentyl-1-aza-3,7-dioxabicyclo[3.3.0]octane, 4-butyl-4-methyl-1-oxa-3-azacyclopentane, 4-ethyl-4-propyl-1-oxa-3-azacyclopentane, 4-hexyl-1-oxa-3-azacyclopentane, 5-hexyl-1-aza-3,7-dioxabicyclo[3.3.0]octane, 4-methyl-4-propyl-1-oxa-3-azacyclopentane, 4,4-dipropyl-1-oxa-3-azacyclopentane, 4-butyl-4-ethyl-1-oxa-3-azacyclopentane, 4-heptyl-1-oxa-3-azacyclopentane, 5-heptyl-1-aza-3,7-dioxabicyclo[3.3.0]octane, 4-hexyl-4-methyl-1-oxa-3-azacyclopentane, 4-ethyl-4-pentyl-1-oxa-3-azacyclopentane, 4-butyl-4-propyl-1-oxa-3-azacyclopentane, 4-octyl-1-oxa-3-azacyclopentane, 5-octyl-1-aza-3,7-dioxabicyclo[3.3.0]octane, 4-heptyl-4-methyl-1-oxa-3-azacyclopentane, 4-ethyl-4-hexyl-1-oxa-3-azacyclopentane, 4-pentyl-4-propyl-1-oxa-3-azacyclopentane, 4,4-dibutyl-1-oxa-3-azacyclopentane, 4-nonyl-1-oxa-3-azacyclopentane, 5-nonyl-1-aza-3,7-dioxabicyclo[3.3.0]octane, 4-methyl-4-octyl-1-oxa-3-azacyclopentane, 4-ethyl-4-heptyl-1-oxa-3-azacyclopentane, 4-hexyl-4-propyl-1-oxa-3-azacyclopentane, 4-butyl-4-pentyl-1-oxa-3-azacyclopentane, 4-decyl-1-oxa-3-azacyclopentane, 5-decyl-1-aza-3,7-dioxabicyclo[3.3.0]octane, 4-methyl-4-nonyl-1-oxa-3-azacyclopentane, 4-heptyl-4-propyl-1-oxa-3-azacyclopentane, 4-ethyl-4-octyl-1-oxa-3-azacyclopentane, 4-butyl-4-hexyl-1-oxa-3-azacyclopentane, 4,4-dipentyl-1-oxa-3-azacyclopentane, 4-undecyl-1-oxa-3-azacyclopentane, 5-undecyl-1-aza-3,7-dioxabicyclo[3.3.0]octane, 4-decyl-4-methyl-1-oxa-3-azacyclopentane, 4-ethyl-4-nonyl-1-oxa-3-azacyclopentane, 4-octyl-4-propyl-1-oxa-3-azacyclopentane, 4-butyl-4-heptyl-1-oxa-3-azacyclopentane, 4-hexyl-4-pentyl-1-oxa-3-azacyclopentane, 4-dodecyl-1-oxa-3-azacyclopentane, 5-dodecyl-1-aza-3,7-dioxabicyclo[3.3.0]octane, 4-methyl-4-undecyl-1-oxa-3-azacyclopentane, 4-decyl-4-ethyl-1-oxa-3-azacyclopentane, 4-nonyl-4-propyl-1-oxa-3-azacyclopentane, 4-butyl-4-octyl-1-oxa-3-azacyclopentane, 4-heptyl-4-pentyl-1-oxa-3-azacyclopentane, 4,4-dihexyl-1-oxa-3-azacyclopentane, 4-tridecyl-1-oxa-3-azacyclopentane, 5-tridecyl-1-aza-3,7-dioxabicyclo[3.3.0]octane, 4-dodecyl-4-methyl-1-oxa-3-azacyclopentane, 4-ethyl-4-undecyl-1-oxa-3-azacyclopentane, 4-decyl-4-propyl-1-oxa-3-azacyclopentane, 4-butyl-4-nonyl-1-oxa-3-azacyclopentane, 4-octyl-4-pentyl-1-oxa-3-azacyclopentane, 4-heptyl-4-hexyl-1-oxa-3-azacyclopentane, 4-tetradecyl-1-oxa-3-azacyclopentane, 5-tetradecyl-1-aza-3,7-dioxabicyclo[3.3.0]octane, 4-methyl-4-tridecyl-1-oxa-3-azacyclopentane, 4-dodecyl-4-ethyl-1-oxa-3-azacyclopentane, 4-propyl-4-undecyl-1-oxa-3-azacyclopentane, 4-butyl-4-decyl-1-oxa-3-azacyclopentane, 4-nonyl-4-pentyl-1-oxa-3-azacyclopentane, 4-hexyl-4-octyl-1-oxa-3-azacyclopentane, 4,4-diheptyl-1-oxa-3-azacyclopentane, 4-pentadecyl-1-oxa-3-azacyclopentane, 5-pentadecyl-1-aza-3,7-dioxabicyclo[3.3.0]octane, 4-methyl-4-tetradecyl-1-oxa-3-azacyclopentane, 4-ethyl-4-tridecyl-1-oxa-3-azacyclopentane, 4-dodecyl-4-propyl-1-oxa-3-azacyclopentane, 4-butyl-4-undecyl-1-oxa-3-azacyclopentane, 4-decyl-4-pentyl-1-oxa-3-azacyclopentane, 4-hexyl-4-nonyl-1-oxa-3-azacyclopentane, 4-heptyl-4-octyl-1-oxa-3-azacyclopentane, 4-hexadecyl-1-oxa-3-azacyclopentane, 5-hexadecyl-1-aza-3,7-dioxabicyclo[3.3.0]octane, 4-methyl-4-pentadecyl-1-oxa-3-azacyclopentane, 4-ethyl-4-tetradecyl-1-oxa-3-azacyclopentane, 4-propyl-4-tridecyl-1-oxa-3-azacyclopentane, 4-butyl-4-dodecyl-1-oxa-3-azacyclopentane, 4-pentyl-4-undecyl-1-oxa-3-azacyclopentane, 4-decyl-4-hexyl-1-oxa-3-azacyclopentane, 4-heptyl-4-nonyl-1-oxa-3-azacyclopentane, 4,4-dioctyl-1-oxa-3-azacyclopentane, 4-heptadecyl-1-oxa-3-azacyclopentane, 5-heptadecyl-1-aza-3,7-dioxabicyclo[3.3.0]octane, 4-hexadecyl-4-methyl-1-oxa-3-azacyclopentane, 4-ethyl-4-pentadecyl-1-oxa-3-azacyclopentane, 4-propyl-4-tetradecyl-1-oxa-3-azacyclopentane, 4-butyl-4-tridecyl-1-oxa-3-azacyclopentane, 4-dodecyl-4-pentyl-1-oxa-3-azacyclopentane, 4-hexyl-4-undecyl-1-oxa-3-azacyclopentane, 4-decyl-4-heptyl-1-oxa-3-azacyclopentane, and 4-octyl-4-nonyl-1-oxa-3-azacyclopentane.

In a fifth embodiment of its third aspect, the invention provides the following hydroxylamines. 2-(hydroxylamino)

hexane, 3-(hydroxylamino)hexane, 2-(hydroxylamino)octane, and 3-(hydroxylamino)octane.

"Alkyl," as used in this specification, encompasses straight and branched chain aliphatic groups having the indicated number of carbon atoms. If no number is indicated (e.g., aryl-alkyl-), then 1-6 alkyl carbons are contemplated. Preferred alkyl groups include, without limitation, methyl, ethyl, propyl, isopropyl, butyl, isobutyl, sec-butyl, tert-butyl, pentyl, hexyl, heptyl, and octyl. Unless otherwise indicated, the alkyl group is optionally substituted with 1, 2, or 3, preferably 1 or 2, more preferably 1, substituents that are compatible with the syntheses described herein. Such substituents include, but are not limited to, nitro, halogen, carboxylic acids (e.g., $C_0$-$C_6$—COOH), and $C_2$-$C_6$ alkene. Unless otherwise indicated, the foregoing substituent groups are not themselves further substituted.

An "aryl" group is a C6-C12 aromatic moiety comprising one to three aromatic rings. Preferably, the aryl group is a C6-C10 aryl group. Preferred aryl include, without limitation, phenyl, naphthyl, anthracenyl, and fluorenyl. More preferred are phenyl and naphthyl. Unless otherwise indicated, the aryl group is optionally substituted with 1, 2, or 3, preferably 1 or 2, more preferably 1, substituents that are compatible with the syntheses described herein. Such substituents include, but are not limited to, $C_1$-$C_6$ alkyl, nitro, halogen, carboxylic acids (e.g., $C_0$-$C_6$—COOH), and $C_2$-$C_6$ alkene. Unless otherwise indicated, the foregoing substituent groups are not themselves further substituted.

The term "cycloalkyl" refers to saturated and partially unsaturated cyclic hydrocarbon groups having the indicated number of ring carbon atoms. If no number is specified, then 3 to 12 carbons, preferably 3 to 8 carbons, and more preferably 3 to 7 carbons, are contemplated. Preferred cycloalkyl groups include, without limitation, cyclopropyl, cyclobutyl, cyclopentyl, cyclopentenyl, cyclohexyl, cyclohexenyl, cycloheptyl, and cyclooctyl. Unless otherwise indicated, the cycloalkyl group is optionally substituted with 1, 2, or 3, preferably 1 or 2, more preferably 1, substituents that are compatible with the syntheses described herein. Such substituents include, but are not limited to, $C_1$-$C_6$ alkyl, nitro, halogen, carboxylic acids (e.g., $C_0$-$C_6$—COOH), and $C_2$-$C_6$ alkene. A preferred substituent is $C_1$-$C_6$ alkyl.

The following examples are illustrative of the invention but are not intended to limit its scope.

EXAMPLES

General. Various aspects of the invention are demonstrated using a lab scale reactor. The reactor is a single tube shell-and-tube heat exchanger with a thermowell located axially down the center of the reactor in order to determine the temperature profile along the reactor's length. The reactor is 46" long and has a shell which is 1.25" OD 304 stainless steel with a ½" OD (0.37" ID) type 2 titanium process tubing and a ⅛" OD (0.093" ID) type 2 titanium thermowell. A very fine, movable thermocouple is inserted into the thermowell for the temperature profile measurement. The thermowell can be removed and the reactor filled with packing. The reactor is mounted vertically. The nitric acid and hydrocarbon reactant streams are mixed in a Swagelok "T" at room temperature prior to entering the reactor. Hot oil used is fed to the reactor shell countercurrent to the reactants. The reactor effluent is cooled in a shell-and-tube heat exchanger using city water as the coolant. The effluent is then depressurized with the gases and liquids collected, measured, and analyzed.

In the examples below, the mass balance of the nitration reaction is determined by GC/MS for gases, aqueous, nitrated hydrocarbons, and scrubber liquids, Karl Fisher titration for water content, potentiometric titration for strong/weak acid quantification, and HPLC for weak acid identification and quantification. Reactant residence times are calculated based on the volume of the reactor divided by the flowrates of the feeds at room temperature and the indicated reaction pressure.

In the Examples, the hydrocarbon compound is nitrated using nitric acid as the nitrating agent. Process conditions as well as key performance measurements are provided in Table 1.

Example 2 (cyclohexane nitration at 600 psi and 210° C.) shows that lower operating pressure tends to reduce raw material conversion and yields. The lower conversion is partially offset by the presence of significantly more nitric oxide which may be recovered as nitric acid. Lower conversion can also be compensated for by increasing the residence time in the reactor.

Example 3 demonstrates the use of packing material in the reactor. Packing increases mixing and heat transfer in the reactor, but also increases the amount of liquid holdup in the reactor which favors increased formation of oxidation byproducts.

Introducing packing significantly increased nitric acid conversion (compared to example 2). However, the low nitric acid and cyclohexane yields show that the increased conversion primarily goes to oxidation byproducts.

The process conditions of Example 8 provide relatively low nitric acid conversion (for n-butane). Examples 9 and 10 demonstrate how the process conditions can be changed to improve the conversion levels.

Example 9 shows that nitric acid conversion is significantly increased (compared to Example 8) by using a higher temperature. The Example also demonstrates that the increase in nitric acid conversion occurs despite the use of less excess n-butane.

Example 10 demonstrates that nitric acid conversion is significantly increased (compared to example 8) by increasing the pressure. This occurs despite the use of less excess n-butane.

Example 11 shows that nitric acid conversion is significantly increased (compared to example 8) by increasing the oil temperature and pressure. In this case the same mole ratio of reactants is used as in Example 8.

TABLE 1

Process Conditions and Key Performance Measurements for Exemplary Hydrocarbons Nitrated According to the Invention.

| Ex | Feed | Pressure (psi) | Temp. (° C.) | Feed:HNO3 (mol) | [HNO3] (wt. %) | Time (s) | NA[a] conversion | HC[b] conversion | NA yield[c] | HC yield[d] |
|---|---|---|---|---|---|---|---|---|---|---|
| 1 | cyclohexane | 1200 | 210 | 2.5:1 | 30 | 120 | 99.9 | 34.8 | 1.01 | 1.28 |
| 2 | cyclohexane | 600 | 210 | 2.0:1 | 30 | 120 | 78.0 | 25.9 | 1.67 | 1.29 |
| 3 | cyclohexane | 600 | 230 | 2.0:1 | 30 | 75 | 100.0 | 32.7 | 2.74 | 2.58 |

TABLE 1-continued

Process Conditions and Key Performance Measurements for Exemplary
Hydrocarbons Nitrated According to the Invention.

| Ex | Feed | Pressure (psi) | Temp. (° C.) | Feed:HNO3 (mol) | [HNO3] (wt. %) | Time (s) | NA[a] conversion | HC[b] conversion | NA yield[c] | HC yield[d] |
|---|---|---|---|---|---|---|---|---|---|---|
| | (packed) | | | | | | | | | |
| 4 | isobutane | 1200 | 210 | 1.65:1 | 30 | 120 | 95.9 | 23.0 | 1.64 | 0.83 |
| 5 | isobutane | 1000 | 220 | 1.3:1 | 30 | 120 | 95.6 | 29.0 | 1.76 | 0.94 |
| 6 | isobutane | 1400 | 200 | 1.3:1 | 30 | 120 | 95.5 | 29.7 | 1.89 | 0.82 |
| 7 | n-butane | 1250 | 220 | 1.6:1 | 30 | 120 | 95.2 | 42.8 | 1.24 | 0.92 |
| 8 | n-butane | 1000 | 200 | 2.0:1 | 30 | 120 | 57.5 | 28.7 | 2.81 | 1.69 |
| 9 | n-butane | 1000 | 240 | 1.2:1 | 30 | 120 | 95.2 | 43.7 | 1.54 | 0.92 |
| 10 | n-butane | 1500 | 200 | 1.2:1 | 30 | 120 | 95.1 | 52.9 | 1.39 | 0.87 |
| 11 | n-butane | 1500 | 240 | 2.0:1 | 30 | 120 | 97.9 | 36.4 | 0.94 | 0.87 |
| 12 | toluene | 900 | 180 | 2.375:1 | 30 | 120 | 71.1 | 28.9 | 1.15 | 1.45 |
| 13 | toluene | 1200 | 160 | 1.75:1 | 30 | 120 | 73.7 | 32.3 | 1.10 | 1.14 |
| 14 | toluene | 1200 | 200 | 3:1 | 30 | 120 | 91.6 | 23.9 | 0.84 | 1.20 |

[a]Nitric Acid Conversion = 100 × (grams nitric acid in − grams nitric acid out)/grams nitric acid in.
[b]HC (hydrocarbon) Conversion = 100 × (grams HC in − grams HC out)/grams HC in.
[c]Nitric Acid Yield = grams nitric acid consumed/grams nitro-HC produced. Grams nitric acid consumed = (moles nitric acid fed − moles NO produced) × 63. This calculation treats unreacted nitric acid as a yield loss.
(Note: 63 g/mole is the molecular weight of nitric acid)
[d]HC yield = grams HC consumed/g nitro-HC produced. Grams HC consumed = grams HC in − grams HC out. This calculation treats unreacted HC as being recoverable.

Additional data for the n-butane nitration examples (Examples 7-11) are provided in Table 2, including selectivity data. 2-Nitrobutane selectivity is calculated as 100×(grams 2-nitrobutane made/(grams 2-nitrobutane made+grams 1-nitrobutane made). The 2-nitrobutane:carboxylic acid weight ratio is calculated as grams 2-nitrobutane/(grams of acetic acid+grams of propionic acid+grams of butyric acid).

TABLE 2

| Ex. | 2-nitrobutane selectivity | 2-nitrobutane:carboxylic acid weight ratio |
|---|---|---|
| 7 | 95.2 | 4.0 |
| 8 | 94.8 | 2.3 |
| 9 | 93.9 | 2.7 |
| 10 | 94.5 | 3.7 |
| 11 | 94.2 | 5.2 |

Table 2 shows the selectivity to 2-nitrobutane is consistent over a wide range of process conditions demonstrating the robustness of the process of the invention.

Further examples of nitrated compounds and process conditions are provided in Table 3.

TABLE 3

| hydrocarbon | residence time, seconds | mole ratio, hydrocarbon:nitric acid | nitric acid strength, wt. % | hot oil temp., C. | pressure, psig | 1-nitro | 2-nitro | 3-nitro | 4-nitro |
|---|---|---|---|---|---|---|---|---|---|
| n-pentane | 120 | 2.5 | 30 | 205 | 1400 | 4.7 | 24.3 | 71.1 | NA |
| n-hexane | 120 | 2.5 | 30 | 200 | 1000 | 3.2 | 49.7 | 47.1 | NA |
| n-octane | 120 | 2 | 30 | 215 | 1000 | 2.1 | 34.2 | 32.1 | 31.6 |
| Isopentane | 120 | 3 | 30 | 180 | 1400 | Mixture of Isomers | | | |
| 3-methyl pentane | 120 | 3 | 30 | 170 | 1400 | Mixture of Isomers | | | |
| 2,3 dimethyl butane | 120 | 3 | 30 | 170 | 1400 | Mixture of Isomers | | | |
| cyclopentane | 120 | 2 | 30 | 220 | 900 | 100% | | | |
| Methylcyclopentane | 120 | 4 | 20 | 190 | 1400 | Mixture of Isomers | | | |
| Methylcyclohexane | 120 | 2 | 30 | 200 | 1200 | Mixture of Isomers | | | |
| Ethylcyclohexane | 120 | 3 | 30 | 185 | 1400 | Mixture of Isomers | | | |
| Isopropylcyclohexane | 120 | 3 | 30 | 185 | 1400 | Mixture of Isomers | | | |
| Tert-butylcyclohexane | 120 | 3 | 30 | 190 | 1400 | Mixture of Isomers | | | |
| cyclooctane | 120 | 2 | 30 | 215 | 1200 | 100% | | | |
| Isooctane | 120 | 2 | 30 | 210 | 1000 | Mixture of Isomers | | | |
| n-hexadecane | 120 | 2 | 30 | 220 | 600 | Mixture of Isomers | | | |
| Tetralin | 120 | 3 | 30 | 155 | 1000 | Mixture of Isomers | | | |
| Decalin | 120 | 3 | 25 | 185 | 1400 | Mixture of Isomers | | | |
| ethylbenzene | 120 | 3 | 30 | 155 | 1500 | * | | | |
| n-Propylbenzene | 120 | 3 | 30 | 175 | 1000 | * | | | |
| Cumene | 90 | 2 | 30 | 140 | 1500 | * | | | |
| Isobutylbenzene | 120 | 2 | 30 | 145 | 1500 | * | | | |

The amounts of 1-nitro, 2-nitro, etc. are the relative amounts of the nitro isomers. The calculation involves summing all of the isomers then determining the distribution using gc area %.
* For aromatic compounds, the nitration occurs exclusively at the carbon next to the ring.

Example 12. Preparation of 1-Nitrooctane

This example is illustrative of an alternative procedure for the preparation of 1-nitroalkanes.

In a 3-neck flask fitted with a stirrer, dropping funnel and reflux condenser protected by a drying tube, are placed 100 g (0.6 5 mol) of silver nitrite and 150 mL anhydrous ether. The mixture is cooled to 0° C. and then, with continuous stirring (in the absence of light), 120 g (0.5 mol) of n-octyl iodide are added over a period of 2 hours. After the addition is complete, the mixture is stirred at 0° C. for 24 hours, followed by stirring at room temperature for an additional 36 hours. The silver salts are removed by filtration and washed with ether. The combined ether solutions is concentrated to an oil which is rectified under reduced pressure. The product boiling between 71.5-72° C./3 torr is collected (64.9 g, 83% yield).

Examples of nitrated compounds that are prepared as described in Examples 1-11 above (using appropriate starting hydrocarbon) are listed in Table 4.

TABLE 4

| Nitrated Compound | Typical Purity (GC) | BP or MP |
|---|---|---|
| 2-nitroisobutane | >98% | water azeotrope 56 C./185 torr (77% nitro/23% water) |
| 2-nitrobutane | Mixture of 1 and 2 isomers | |
| 2-nitropentane | Nearly 1:1 mixture of 2,3 isomers (>98.5% by GC) | 58 C./10 torr |
| 3-nitrohexane | Mixture 2,3-isomers | 56-58 C./9.5 torr |
| 4-nitrooctane | Mixture of 2,3,4 isomers (>99.5% by GC) | 66-76° C./4 torr |
| 1-nitrocyclopentane | 95-99% | 76° C./19 torr |
| 1-nitrocyclohexane | >98% | |
| 1-nitrocyclooctane | 92% nitrocyclooctane, 5% nitrocyclooctene | 76 C./1.2 torr |
| phenylnitromethane | 90% + contaminants | 83° C./2.3 torr |
| 1,1,3,3-tetramethylnitrobutane | Mixture of nitroisomers | |
| 1-methyl-1-nitrocyclopentane | 80% + isomers | |
| 1-methyl-1-nitrocyclohexane | 60% + isomers | 46-59° C./1 torr |
| 1-phenylnitroethane | >97% | 95/2 torr |
| 2-phenyl-2-nitropropane | >70% | 90 C./0.3 torr |

Following the procedures described above and making non-critical variations, the following additional nitrated compounds are prepared from the appropriate starting hydrocarbon (Table 5).

TABLE 5

| Nitrated Compound |
|---|
| 1-nitroisobutane |
| 1-nitrobutane |
| 1-nitropentane |
| 3-nitropentane |
| 1-nitrohexane |
| 2-nitrohexane |
| 1-nitroheptane |
| 2-nitroheptane |
| 3-nitroheptane |
| 4-nitroheptane |
| 1-nitrooctane |
| 2-nitrooctane |
| 3-nitrooctane |
| 1-nitrononane |
| 2-nitrononane |

TABLE 5-continued

| Nitrated Compound |
|---|
| 3-nitrononane |
| 4-nitrononane |
| 5-nitrononane |
| 1-nitrodecane |
| 2-nitrodecane |
| 3-nitrodecane |
| 4-nitrodecane |
| 5-nitrodecane |
| 1-nitroundecane |
| 2-nitroundecane |
| 3-nitroundecane |
| 4-nitroundecane |
| 5-nitroundecane |
| 6-nitroundecane |
| 1-nitrododecane |
| 2-nitrododecane |
| 3-nitrododecane |
| 4-nitrododecane |
| 5-nitrododecane |
| 6-nitrododecane |
| 1-nitrotridecane |
| 2-nitrotridecane |
| 3-nitrotridecane |
| 4-nitrotridecane |
| 5-nitrotridecane |
| 6-nitrotridecane |
| 7-nitrotridecane |
| 1-nitrotetradecane |
| 2-nitrotetradecane |
| 3-nitrotetradecane |
| 4-nitrotetradecane |
| 5-nitrotetradecane |
| 6-nitrotetradecane |
| 7-nitrotetradecane |
| 1-nitropentadecane |
| 2-nitropentadecane |
| 3-nitropentadecane |
| 4-nitropentadecane |
| 5-nitropentadecane |
| 6-nitropentadecane |
| 7-nitropentadecane |
| 8-nitropentadecane |
| 1-nitrohexadecane |
| 2-nitrohexadecane |
| 3-nitrohexadecane |
| 4-nitrohexadecane |
| 5-nitrohexadecane |
| 6-nitrohexadecane |
| 7-nitrohexadecane |
| 8-nitrohexadecane |
| 1-nitroheptadecane |
| 2-nitroheptadecane |
| 3-nitroheptadecane |
| 4-nitroheptadecane |
| 5-nitroheptadecane |
| 6-nitroheptadecane |
| 7-nitroheptadecane |
| 8-nitroheptadecane |
| 9-nitroheptadecane |
| 1-nitrooctadecane |
| 2-nitrooctadecane |
| 3-nitrooctadecane |
| 4-nitrooctadecane |
| 5-nitrooctadecane |
| 6-nitrooctadecane |
| 7-nitrooctadecane |
| 8-nitrooctadecane |
| 9-nitrooctadecane |
| phenylnitromethane |
| naphthylnitromethane |
| nitromethylbiphenyl |
| 2-methyl-2-nitrobutane |
| 3-nitropropylbenzene |

Example 13. Preparation of 2-Methyl-2-Nitro-1-Butanol

A 2-liter 3-neck flask is equipped with a mechanical stirrer, a reflux condenser with a nitrogen bubbler, an addition funnel and a temperature controller with heating mantle and thermocouple. The flask is charged with aqueous formaldehyde solution (420 mL, 37% active, 5.64 mol) and 4 mL triethylamine catalyst. The addition funnel is charged with 2-nitrobutane (554.1 g, 5.37 mol). The 2-nitrobutane is added dropwise, over a period of 7 hours to the formaldehyde solution, which is being stirred under nitrogen. The reaction is maintained at 40° C. during the addition. After all the 2-nitrobutane is added, the turbid mixture is warmed to 45° C. for 30 min, and then heating and stirring are discontinued overnight. If a GC analysis indicates the reaction is not yet complete; an additional 10.9 g aqueous formaldehyde is added and the mixture stirred at 45° C. for 2.5 hours. Upon cooling to room temperature, the reaction mass separates into an oil layer with a smaller, separate water layer. The oil layer is collected (1022.8 g, 97.9% of theory) and GC indicates 94.8% purity. The oil is used without further purification.

Additional examples of nitroalcohols that are prepared as described above (substituting the appropriate starting materials) are listed in Table 6.

TABLE 6

| Nitroalcohol | Typical Purity (area % GC or LC) | BP or MP |
|---|---|---|
| 2-methyl-2-nitro-1-butanol | 95% | |
| 2-ethyl-2-nitro-1-pentanol | Mixture with 2-methyl-2-nitro-1-hexanol: 93% by GC | |
| 2-nitro-2-propyl-1-hexanol | Mixture of 2,3,4-isomers | |
| 1-hydroxymethyl-1-nitrocyclopentane | 93.5% | |
| 1-hydroxymethyl-1-nitrocyclohexane | 95% | |
| 1-hydroxymethyl-1-nitrocyclooctane | 51% | |
| (1,1-bis-hydroxymethyl-1-nitromethyl)benzene | >99% | Mp = 96.4° C. |
| 2-nitro-2-phenyl-1-propanol | 86.5% (LC) | Mp = 52-53 C. |

Following the procedures described above and making non-critical variations, the following additional nitroalcohols are prepared from the appropriate starting hydrocarbon (Table 7).

TABLE 7

| Nitroalcohol |
|---|
| 2-nitro-1-pentanol |
| 2-hydroxymethyl-2-nitro-1-pentanol |
| 2-nitro-1-hexanol |
| 2-hydroxymethyl-2-nitro-1-hexanol |
| 2-methyl-2-nitro-1-pentanol |
| 2-ethyl-2-nitro-1-butanol |
| 2-nitro-1-heptanol |
| 2-hydroxymethyl-2-nitro-1-heptanol |
| 2-methyl-2-nitro-1-hexanol |
| 2-nitro-1-octanol |
| 2-hydroxymethyl-2-nitro-1-octanol |
| 2-methyl-2-nitro-1-heptanol |
| 2-ethyl-2-nitro-1-hexanol |
| 2-nitro-2-propyl-1-pentanol |
| 2-nitro-1-nonanol |
| 2-hydroxymethyl-2-nitro-1-nonanol |
| 2-methyl-2-nitro-1-octanol |
| 2-ethyl-2-nitro-1-heptanol |

TABLE 7-continued

| Nitroalcohol |
|---|
| 2-nitro-1-decanol |
| 2-hydroxymethyl-2-nitro-1-decanol |
| 2-methyl-2-nitro-1-nonanol |
| 2-ethyl-2-nitro-1-octanol |
| 2-nitro-2-propyl-1-heptanol |
| 2-butyl-2-nitro-1-hexanol |
| 2-nitro-1-undecanol |
| 2-hydroxymethyl-2-nitro-1-undecanol |
| 2-methyl-2-nitro-1-decanol |
| 2-ethyl-2-nitro-1-nonanol |
| 2-propyl-2-nitro-1-octanol |
| 2-butyl-2-nitro-1-heptanol |
| 2-nitro-1-dodecanol |
| 2-hydroxymethyl-2-nitro-1-dodecanol |
| 2-methyl-2-nitro-1-undecanol |
| 2-ethyl-2-nitro-1-decanol |
| 2-propyl-2-nitro-1-nonanol |
| 2-butyl-2-nitro-1-octanol |
| 2-pentyl-2-nitro-1-heptanol |
| 2-nitro-1-tridecanol |
| 2-hydroxymethyl-2-nitro-1-tridecanol |
| 2-methyl-2-nitro-1-dodecanol |
| 2-ethyl-2-nitro-1-undecanol |
| 2-propyl-2-nitro-1-decanol |
| 2-butyl-2-nitro-1-nonanol |
| 2-pentyl-2-nitro-1-octanol |
| 2-nitro-1-tetradecanol |
| 2-hydroxymethyl-2-nitro-1-tetradecanol |
| 2-methyl-2-nitro-1-tridecanol |
| 2-ethyl-2-nitro-1-dodecanol |
| 2-propyl-2-nitro-1-undecanol |
| 2-butyl-2-nitro-1-decanol |
| 2-pentyl-2-nitro-1-nonanol |
| 2-hexyl-2-nitro-1-octanol |
| 2-nitro-1-pentadecanol |
| 2-hydroxymethyl-2-nitro-1-pentadecanol |
| 2-methyl-2-nitro-1-tetradecanol |
| 2-ethyl-2-nitro-1-tridecanol |
| 2-propyl-2-nitro-1-dodecanol |
| 2-butyl-2-nitro-1-undecanol |
| 2-pentyl-2-nitro-1-decanol |
| 2-hexyl-2-nitro-1-nonanol |
| 2-heptyl-2-nitro-1-octanol |
| 2-nitro-1-hexadecanol |
| 2-hydroxymethyl-2-nitro-1-hexadecanol |
| 2-methyl-2-nitro-1-pentadecanol |
| 2-ethyl-2-nitro-1-tetradecanol |
| 2-propyl-2-nitro-1-tridecanol |
| 2-butyl-2-nitro-1-dodecanol |
| 2-pentyl-2-nitro-1-undecanol |
| 2-hexyl-2-nitro-1-decanol |
| 2-heptyl-2-nitro-1-nonanol |
| 2-nitro-1-heptadecanol |
| 2-hydroxymethyl-2-nitro-1-heptadecanol |
| 2-methyl-2-nitro-1-hexadecanol |
| 2-ethyl-2-nitro-1-pentadecanol |
| 2-propyl-2-nitro-1-tetradecanol |
| 2-butyl-2-nitro-1-tridecanol |
| 2-pentyl-2-nitro-dodecanol |
| 2-hexyl-2-nitro-1-undecanol |
| 2-heptyl-2-nitro-1-decanol |
| 2-nitro-1-octadecanol |
| 2-hydroxymethyl-2-nitro-1-octadecanol |
| 2-methyl-2-nitro-1-heptadecanol |
| 2-ethyl-2-nitro-1-hexadecanol |
| 2-propyl-2-nitro-1-pentadecanol |
| 2-butyl-2-nitro-1-tetradecanol |
| 2-pentyl-2-nitro-1-tridecanol |
| 2-hexyl-2-nitro-1-dodecanol |
| 2-heptyl-2-nitro-1-undecanol |
| 2-octyl-2-nitro-1-decanol |
| 2-nitro-1-nonadecanol |
| 2-hydroxymethyl-2-nitro-1-nonadecanol |
| 2-methyl-2-nitro-1-octadecanol |
| 2-ethyl-2-nitro-1-heptadecanol |
| 2-propyl-2-nitro-1-hexadecanol |
| 2-butyl-2-nitro-1-pentadecanol |
| 2-pentyl-2-nitro-1-tetradecanol |

TABLE 7-continued

| Nitroalcohol |
| --- |
| 2-hexyl-2-nitro-1-tridecanol |
| 2-heptyl-2-nitro-1-dodecanol |
| 2-octyl-2-nitro-1-undecanol |

Example 14. Preparation of 2-Amino-2-Methyl-1-Butanol

A 2-liter Parr autoclave is charged with methanol (300 mL) and Raney Nickel catalyst (R-3111 grade, 26.5 g wet weight). The reactor is sealed, purged with nitrogen followed by purging with hydrogen and then brought up to 65° C. under 625 psi hydrogen pressure. With rapid stirring, a solution of 2-nitro-2-methyl-1-butanol in water (450 g total solution, 71% actives) is added over 1.5 hours while maintaining 65° C./610 psi hydrogen. When the addition is completed, the reaction is allowed to continue for an additional 10 minutes followed by cooling to room temperature. The autoclave is vented, opened and the crude product isolated via vacuum filtration. The methanol solvent is removed on a rotary evaporator at 50° C./29" vacuum, followed by azeotropically removing the last remnants of water with 100 mL toluene under identical conditions. The yield of crude, stripped product is 196.6 g (79% of theory). The product is vacuum distilled through a fractionating column packed with stainless steel mesh; the product boiling between 85-86° C./15 torr is collected. GC analysis indicates >97% purity for the water white oil.

Additional examples of aminoalcohols that are prepared as described above (substituting the appropriate starting materials) are listed in Table 8.

TABLE 8

| Aminoalcohol | Typical Purity (GC) | BP or MP |
| --- | --- | --- |
| 2-amino-2-methyl-1-butanol | 97.8% | 85-86° C./15 torr |
| 2-amino-2-methyl-1-hexanol | Mixture with 2-amino-2-ethyl-1-pentanol. 96% | 103-106 C./15 mm |
| 2-amino-2-propyl-1-hexanol | Mixture of 2,3,4 isomers. 92.2% | 99 C./2.2 mm |
| 1-hydroxymethyl-1-aminocyclopentane | 96.6% | 111-112 C./15 mm |
| 1-hydroxymethyl-1-aminocyclohexane | 98.6% | 106-108 C./7 torr |
| 1-hydroxymethyl-1-aminocycloheptane | | |
| 1-hydroxymethyl-1-aminocyclooctane | 71.5% | 139-141 C./9 mm (mp = 40-50 C.) |
| (1,1-bis-hydroxymethyl-1-aminomethyl)benzene | >99% | Mp = 117.4° C. |
| 2-amino-2-phenyl-1-propanol | 79% | 115-121 C./2.2 mm |

Following the procedures described above and making non-critical variations, the following additional aminoalcohol compounds are prepared from the appropriate starting materials (Table 9).

TABLE 9

| Aminoalcohol |
| --- |
| 2-amino-1-pentanol |
| 2-amino-2-propyl-1,3-propanediol |
| 2-amino-1-hexanol |
| 2-amino-2-butyl-1,3-propanediol |
| 2-amino-2-methyl-1-pentanol |

TABLE 9-continued

| Aminoalcohol |
| --- |
| 2-amino-2-ethyl-1-butanol |
| 2-amino-1-heptanol |
| 2-amino-2-pentyl-1,3-propanediol |
| 2-amino-2-ethyl-1-pentanol |
| 2-amino-1-octanol |
| 2-amino-2-hexyl-1,3-propanediol |
| 2-amino-2-methyl-1-heptanol |
| 2-amino-2-ethyl-1-hexanol |
| 2-amino-2-propyl-1-pentanol |
| 2-amino-1-nonanol |
| 2-amino-2-heptyl-1,3-propanediol |
| 2-amino-2-methyl-1-octanol |
| 2-amino-2-ethyl-1-heptanol |
| 2-amino-1-decanol |
| 2-amino-2-octyl-1,3-propanediol |
| 2-amino-2-methyl-1-nonanol |
| 2-amino-2-ethyl-1-octanol |
| 2-amino-2-propyl-1-heptanol |
| 2-amino-2-butyl-1-hexanol |
| 2-amino-1-undecanol |
| 2-amino-2-nonyl-1,3-propanediol |
| 2-amino-2-methyl-1-decanol |
| 2-amino-2-ethyl-1-nonanol |
| 2-amino-2-propyl-1-octanol |
| 2-amino-2-butyl-1-heptanol |
| 2-amino-1-dodecanol |
| 2-amino-2-decyl-1,3-propanediol |
| 2-amino-2-methyl-1-undecanol |
| 2-amino-2-ethyl-1-decanol |
| 2-amino-2-propyl-1-nonanol |
| 2-amino-2-butyl-1-octanol |
| 2-amino-2-pentyl-1-heptanol |
| 2-amino-1-tridecanol |
| 2-amino-2-undecyl-1,3-propanediol |
| 2-amino-2-methyl-1-dodecanol |
| 2-amino-2-ethyl-1-undecanol |
| 2-amino-2-propyl-1-decanol |
| 2-amino-2-butyl-1-nonanol |
| 2-amino-2-pentyl-1-octanol |
| 2-amino-1-tetradecanol |
| 2-amino-2-dodecyl-1,3-propanediol |
| 2-amino-2-methyl-1-tridecanol |
| 2-amino-2-ethyl-1-dodecanol |
| 2-amino-2-propyl-1-undecanol |
| 2-amino-2-butyl-1-decanol |
| 2-amino-2-pentyl-1-nonanol |
| 2-amino-2-hexyl-1-octanol |
| 2-amino-1-pentadecanol |
| 2-amino-2-tridecyl-1,3-propanediol |
| 2-amino-2-methyl-1-tetradecanol |
| 2-amino-2-ethyl-1-tridecanol |
| 2-amino-2-propyl-1-dodecanol |
| 2-amino-2-butyl-1-undecanol |
| 2-amino-2-pentyl-1-decanol |
| 2-amino-2-hexyl-1-nonanol |
| 2-amino-1-hexadecanol |
| 2-amino-2-tetradecyl-1,3-propanediol |
| 2-amino-2-methyl-1-pentadecanol |
| 2-amino-2-ethyl-1-tetradecanol |
| 2-amino-2-propyl-1-tridecanol |
| 2-amino-2-butyl-1-dodecanol |
| 2-amino-2-pentyl-1-undecanol |
| 2-amino-2-hexyl-1-decanol |
| 2-amino-2-heptyl-1-nonanol |
| 2-amino-1-heptadecanol |
| 2-amino-2-pentadecyl-1,3-propanediol |
| 2-amino-2-methyl-1-hexadecanol |
| 2-amino-2-ethyl-1-pentadecanol |
| 2-amino-2-propyl-1-tetradecanol |
| 2-amino-2-butyl-1-tridecanol |
| 2-amino-2-pentyl-1-dodecanol |
| 2-amino-2-hexyl-1-undecanol |
| 2-amino-2-heptyl-1-decanol |
| 2-amino-1-octadecanol |
| 2-amino-2-hexadecyl-1,3-propanediol |
| 2-amino-2-methyl-1-heptadecanol |
| 2-amino-2-ethyl-1-hexadecanol |
| 2-amino-2-propyl-1-pentadecanol |

TABLE 9-continued

Aminoalcohol 2-amino-2-butyl-1-tetradecanol
2-amino-2-pentyl-1-tridecanol
2-amino-2-hexyl-1-dodecanol
2-amino-2-heptyl-1-undecanol
2-amino-2-octyl-1-decanol
2-amino-1-nonadecanol
2-amino-2-heptadecyl-1,3-propanediol
2-amino-2-methyl-1-octadecanol
2-amino-2-ethyl-1-heptadecanol
2-amino-2-propyl-1-hexadecanol
2-amino-2-butyl-1-pentadecanol
2-amino-2-pentyl-1-tetradecanol
2-amino-2-hexyl-1-tridecanol
2-amino-2-heptyl-1-dodecanol
2-amino-2-octyl-1-undecanol
1-hydroxymethyl-1-aminocyclononane
1-hydroxymethyl-1-aminocyclodecane
1-hydroxymethyl-1-aminocyclooundecane
1-hydroxymethyl-1-aminocyclododecane Example 15. Preparation of 3-Oxa-1-azaspiro[4.5]decane To a 500 mL flask containing 1-amino-cyclohexylmethanol (135 g, 1.05 mol) and methanol (50 mL) is added methyl formcel (53 mL of 55% formaldehyde in methanol/water, 1.06 mol) dropwise over a 1 hour period. During the addition, the stirred solution is warmed gently from room temperature to 37° C. After the addition is completed, the mixture is allowed to stir overnight at room temperature. The clear, colorless reaction mixture is stripped on a rotary evaporator (50° C./29″ vacuum). The resulting oil is distilled under vacuum giving a clear, colorless, mobile liquid with a boiling point of 43° C./0.8 torr. A total of 123.4 g is collected (83% yield). A GC analysis indicates 95.6% purity.

Following the procedures described above and making non-critical variations, the following oxazolidine compounds are prepared from the appropriate starting aminoalcohol (Table 10).

TABLE 10

| Oxazolidine | Starting Aminoalcohol |
| --- | --- |
| 4-propyl-1-oxa-3-azacyclopentane | 2-amino-1-pentanol |
| 5-propyl-1-aza-3,7-dioxabicyclo[3.3.0]octane | 2-amino-2-hydroxymethyl-1-pentanol |
| 4-ethyl-4-methyl-1-oxa-3-azacyclopentane | 2-amino-2-methyl-1-butanol |
| 4-butyl-1-oxa-3-azacyclopentane | 2-amino-1-hexanol |
| 5-butyl-1-aza-3,7-dioxabicyclo[3.3.0]octane | 2-amino-2-hydroxymethyl-1-hexanol |
| 4-propyl-4-methyl-1-oxa-3-azacyclopentane | 2-amino-2-methyl-1-pentanol |
| 4,4-diethyl-1-oxa-3-azacyclopentane | 2-amino-2-ethyl-1-butanol |
| 4-pentyl-1-oxa-3-azacyclopentane | 2-amino-1-heptanol |
| 5-pentyl-1-aza-3,7-dioxabicyclo[3.3.0]octane | 2-amino-2-hydroxymethyl-1-heptanol |
| 4-butyl-4-methyl-1-oxa-3-azacyclopentane | 2-amino-2-methyl-1-hexanol |
| 4-ethyl-4-propyl-1-oxa-3-azacyclopentane | 2-amino-2-ethyl-1-pentanol |
| 4-hexyl-1-oxa-3-azacyclopentane | 2-amino-1-octanol |
| 5-hexyl-1-aza-3,7-dioxabicyclo[3.3.0]octane | 2-amino-2-hydroxymethyl-1-octanol |
| 4-methyl-4-propyl-1-oxa-3-azacyclopentane | 2-amino-2-methyl-1-heptanol |
| 4,4-dipropyl-1-oxa-3-azacyclopentane | 2-amino-2-ethyl-1-hexanol |
| 4-butyl-4-ethyl-1-oxa-3-azacyclopentane | 2-amino-2-propyl-1-pentanol |
| 4-heptyl-1-oxa-3-azacyclopentane | 2-amino-1-nonanol |
| 5-heptyl-1-aza-3,7-dioxabicyclo[3.3.0]octane | 2-amino-2-hydroxymethyl-1-nonanol |
| 4-hexyl-4-methyl-1-oxa-3-azacyclopentane | 2-amino2-methyl-1-octanol |
| 4-ethyl-4-pentyl-1-oxa-3-azacyclopentane | 2-amino-2-ethyl-1-heptanol |
| 4-butyl-4-propyl-1-oxa-3-azacyclopentane | 2-amino-2-propyl-1-hexanol |
| 4-octyl-1-oxa-3-azacyclopentane | 2-amino-1-decanol |
| 5-octyl-1-aza-3,7-dioxabicyclo[3.3.0]octane | 2-amino-2-hydroxymethyl-1-decanol |
| 4-heptyl-4-methyl-1-oxa-3-azacyclopentane | 2-amion-2-methyl-1-nonanol |
| 4-ethyl-4-hexyl-1-oxa-3-azacyclopentane | 2-amion-2-ethyl-1-octanol |
| 4-pentyl-4-propyl-1-oxa-3-azacyclopentane | 2-amino-2-propyl-1-heptanol |
| 4,4-dibutyl-1-oxa-3-azacyclopentane | 2-amino-2-butyl-1-hexanol |
| 4-nonyl-1-oxa-3-azacyclopentane | 2-amino-1-undecanol |
| 5-nonyl-1-aza-3,7-dioxabicyclo[3.3.0]octane | 2-amino-2-hydroxymethy-1-undecanol |
| 4-methyl-4-octyl-1-oxa-3-azacyclopentane | 2-amino-2-methyl-1-decanol |
| 4-ethyl-4-heptyl-1-oxa-3-azacyclopentane | 2-amino-2-ethyl-1-nonanol |
| 4-hexyl-4-propyl-1-oxa-3-azacyclopentane | 2-amino-2-propyl-1-octanol |
| 4-butyl-4-pentyl-1-oxa-3-azacyclopentane | 2-amino-2-butyl-1-heptanol |
| 4-decyl-1-oxa-3-azacyclopentane | 2-amino-1-dodecanol |
| 5-decyl-1-aza-3,7-dioxabicyclo[3.3.0]octane | 2-amino-2-hydroxymethy-1-dodecanol |
| 4-methyl-4-nonyl-1-oxa-3-azacyclopentane | 2-amino-2-methyl-1-undecanol |
| 4-heptyl-4-propyl-1-oxa-3-azacyclopentane | 2-amino-2-ethyl-1-decanol |
| 4-ethyl-4-octyl-1-oxa-3-azacyclopentane | 2-amino-2-propyl-1-nonanol |
| 4-butyl-4-hexyl-1-oxa-3-azacyclopentane | 2-amino-2-butyl-1-octanol |
| 4,4-dipentyl-1-oxa-3-azacyclopentane | 2-amino-2-pentyl-1-heptanol |
| 4-undecyl-1-oxa-3-azacyclopentane | 2-amino-1-tridecanol |
| 5-undecyl-1-aza-3,7-dioxabicyclo[3.3.0]octane | 2-amino-2-hydroxymethyl-1-tridecanol |
| 4-decyl-4-methyl-1-oxa-3-azacyclopentane | 2-amino-2-methyl-1-dodecanol |
| 4-ethyl-4-nonyl-1-oxa-3-azacyclopentane | 2-amino-2-ethyl-1-undecanol |
| 4-octyl-4-propyl-1-oxa-3-azacyclopentane | 2-amino-2-propyl-1-decanol |
| 4-butyl-4-heptyl-1-oxa-3-azacyclopentane | 2-amino-2-butyl-1-nonanol |
| 4-hexyl-4-pentyl-1-oxa-3-azacyclopentane | 2-amino-2-pentyl-1-octanol |
| 4-dodecyl-1-oxa-3-azacyclopentane | 2-amino-1-tetradecanol |
| 5-dodecyl-1-aza-3,7-dioxabicyclo[3.3.0]octane | 2-amino-2-hydroxymethyl-1-tetradecanol |
| 4-methyl-4-undecyl-1-oxa-3-azacyclopentane | 2-amino-2-methyl-1-tridecanol |
| 4-decyl-4-ethyl-1-oxa-3-azacyclopentane | 2-amino-2-ethyl-1-dodecanol |

TABLE 10-continued

| Oxazolidine | Starting Aminoalcohol |
|---|---|
| 4-nonyl-4-propyl-1-oxa-3-azacyclopentane | 2-amino-2-propyl-1-undecanol |
| 4-butyl-4-octyl-1-oxa-3-azacyclopentane | 2-amino-2-butyl-1-decanol |
| 4-heptyl-4-pentyl-1-oxa-3-azacyclopentane | 2-amino-2-pentyl-1-nonanol |
| 4,4-dihexyl-1-oxa-3-azacyclopentane | 2-amino-2-hexyl-1-octanol |
| 4-tridecyl-1-oxa-3-azacyclopentane | 2-amino-1-pentadecanol |
| 5-tridecyl-1-aza-3,7-dioxabicyclo[3.3.0]octane | 2-amino-2-hydroxymethyl-1-pentadecanol |
| 4-dodecyl-4-methyl-1-oxa-3-azacyclopentane | 2-amino-2-methyl-1-tetradecanol |
| 4-ethyl-4-undecyl-1-oxa-3-azacyclopentane | 2-amino-2-ethyl-1-tridecanol |
| 4-decyl-4-propyl-1-oxa-3-azacyclopentane | 2-amino-2-propyl-1-dodecanol |
| 4-butyl-4-nonyl-1-oxa-3-azacyclopentane | 2-amino-2-butyl-1-undecanol |
| 4-octyl-4-pentyl-1-oxa-3-azacyclopentane | 2-amino-2-pentyl-1-decanol |
| 4-heptyl-4-hexyl-1-oxa-3-azacyclopentane | 2-amino-2-hexyl-1-nonanol |
| 4-tetradecyl-1-oxa-3-azacyclopentane | 2-amino-1-hexadecanol |
| 5-tetradecyl-1-aza-3,7-dioxabicyclo[3.3.0]octane | 2-amino-2-hydroxymethyl-1-hexadecanol |
| 4-methyl-4-tridecyl-1-oxa-3-azacyclopentane | 2-amino-2-methyl-1-pentadecanol |
| 4-dodecyl-4-ethyl-1-oxa-3-azacyclopentane | 2-amino-2-ethyl-1-tetradecanol |
| 4-propyl-4-undecyl-1-oxa-3-azacyclopentane | 2-amino-2-propyl-1-tridecanol |
| 4-butyl-4-decyl-1-oxa-3-azacyclopentane | 2-amino-2-butyl-1-dodecanol |
| 4-nonyl-4-pentyl-1-oxa-3-azacyclopentane | 2-amino-2-pentyl-1-undecanol |
| 4-hexyl-4-octyl-1-oxa-3-azacyclopentane | 2-amino-2-hexyl-1-decanol |
| 4,4-diheptyl-1-oxa-3-azacyclopentane | 2-amino-2-heptyl-1-nonanol |
| 4-pentadecyl-1-oxa-3-azacyclopentane | 2-amino-1-heptadecanol |
| 5-pentadecyl-1-aza-3,7-dioxabicyclo[3.3.0]octane | 2-amino-2-hydroxymethyl-1-heptadecanol |
| 4-methyl-4-tetradecyl-1-oxa-3-azacyclopentane | 2-amino-2-methyl-1-hexadecanol |
| 4-ethyl-4-tridecyl-1-oxa-3-azacyclopentane | 2-amino-2-ethyl-1-pentadecanol |
| 4-dodecyl-4-propyl-1-oxa-3-azacyclopentane | 2-amino-2-propyl-1-tetradecanol |
| 4-butyl-4-undecyl-1-oxa-3-azacyclopentane | 2-amino-2-butyl-1-tridecanol |
| 4-decyl-4-pentyl-1-oxa-3-azacyclopentane | 2-amino-2-pentyl-1-dodecanol |
| 4-hexyl-4-nonyl-1-oxa-3-azacyclopentane | 2-amino-2-hexyl-1-undecanol |
| 4-heptyl-4-octyl-1-oxa-3-azacyclopentane | 2-amino-2-heptyl-1-decanol |
| 4-hexadecyl-1-oxa-3-azacyclopentane | 2-amino-1-octadecanol |
| 5-hexadecyl-1-aza-3,7-dioxabicyclo[3.3.0]octane | 2-amino-2-hydroxymethyl-1-octadecanol |
| 4-methyl-4-pentadecyl-1-oxa-3-azacyclopentane | 2-amino-2-methyl-heptadecanol |
| 4-ethyl-4-tetradecyl-1-oxa-3-azacyclopentane | 2-amino-2-ethyl-1-hexadecanol |
| 4-propyl-4-tridecyl-1-oxa-3-azacyclopentane | 2-amino-2-propyl-1-pentadecanol |
| 4-butyl-4-dodecyl-1-oxa-3-azacyclopentane | 2-amino-2-butyl-2-tetradecanol |
| 4-pentyl-4-undecyl-1-oxa-3-azacyclopentane | 2-amino-2-pentyl-1-tridecanol |
| 4-decyl-4-hexyl-1-oxa-3-azacyclopentane | 2-amino-2-hexyl-1-dodecanol |
| 4-heptyl-4-nonyl-1-oxa-3-azacyclopentane | 2-amino-2-heptyl-1-undecanol |
| 4,4-dioctyl-1-oxa-3-azacyclopentane | 2-amino-2-octyl-1-decanol |
| 4-heptadecyl-1-oxa-3-azacyclopentane | 2-amino-1-nonadecanol |
| 5-heptadecyl-1-aza-3,7-dioxabicyclo[3.3.0]octane | 2-amino-2-hydroxymethyl-1-nonadecanol |
| 4-hexadecyl-4-methyl-1-oxa-3-azacyclopentane | 2-amino-2-methyl-1-octadecanol |
| 4-ethyl-4-pentadecyl-1-oxa-3-azacyclopentane | 2-amino-2-ethyl-1-heptadecanol |
| 4-propyl-4-tetradecyl-1-oxa-3-azacyclopentane | 2-amino-2-propyl-1-hexadecanol |
| 4-butyl-4-tridecyl-1-oxa-3-azacyclopentane | 2-amino-2-butyl-2-pentadecanol |
| 4-dodecyl-4-pentyl-1-oxa-3-azacyclopentane | 2-amino-2-pentyl-1-tetradecanol |
| 4-hexyl-4-undecyl-1-oxa-3-azacyclopentane | 2-amino-2-hexyl-1-tridecanol |
| 4-decyl-4-heptyl-1-oxa-3-azacyclopentane | 2-amino-2-heptyl-1-dodecanol |
| 4-octyl-4-nonyl-1-oxa-3-azacyclopentane | 2-amino-2-octyl-1-undecanol |
| 3-oxa-1-azaspiro[4.4]nonane | 1-amino-1-hydroxymethylcyclopentane |
| 3-oxa-1-azaspiro[4.5]decane | 1-amino-1-hydroxymethylcyclohexane |
| 3-oxa-1-azaspiro[4.7]dodecane | 1-amino-1-hydroxymethylcyclooctane |

Example 16. Use of Oxazolidine Derivatives as Phenolic Resin Curing Agents

DSC Analyses:

DSC analyses are performed using a TA Instruments Model Q100 differential scanning calorimeter. Scans for screening hardeners with novolac resins are run from 25° C. to 250° C. at ΔT=10° C./minute with a nitrogen flow of 50 cc/minute. High volume (100 μL) aluminum pans are used. A small hole is punched in the top before crimping. After the initial scan, the samples are cooled back to room temperature, then the scans are re-run to obtain $T_g$ data.

In order to demonstrate the utility of the oxazolidines of the methods and/or compounds of the invention as hardeners, a series of formulations are prepared using commercially available PF novolac resins. In order to facilitate mixing of components, the resins in this study are used as 80 wt. % solutions in ethanol. Any variations observed in the curing behavior of these formulations are attributed to the hardener/catalyst being evaluated. ZOLDINE™ ZE, structure shown below, is used as the baseline for comparison since it is a known curing agent for phenolic novolac resins. The formulations are adjusted to keep the molar ratio of hardener to phenolic resin reactive sites constant.

The formulations are evaluated using a differential scanning calorimeter (DSC; TA Instruments Model Q100) to observe curing onset and peak temperatures and heats of curing for the curing events taking place. The DSC scans are run at ΔT=10° C./minute from 25° C. to 250° C. under a nitrogen flow of 50 cc/minute. The data obtained in this study are summarized in Table 11 below.

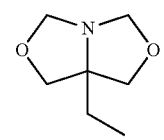

Zoldine ZE
(comparative)

Compound A
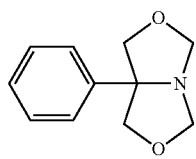
(inventive)

Compound B
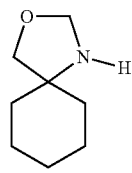
(inventive)

Compound C
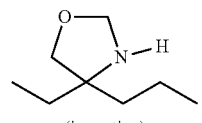
(inventive)

Compound D
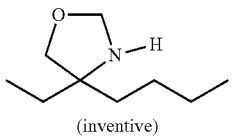
(inventive)

TABLE 11

| Example # | Hardener | PHR | Onset/Peak 1 (Heat J/g) | Onset/Peak 2 (Heat J/g) | Observations After Cure |
|---|---|---|---|---|---|
| Baseline 1 (comparative) | ZE | 33.3 | 166/194 (264) | None | No exotherm, Tg > 200 C. |
| Baseline 2 (comparative) | ZE | 44.2 | 171/198 (244 | None | No exotherm, Tg > 200 C. |
| Example 16-1 | Compound A | 48 | 58.1/96.5 (28.8) | 202/224.1 (161.2) | No exotherm, Tg = 110 C. |
| Example 16-2 | Compound B | 72 | 55/193.5 (129.2) | None | No exotherm, Tg = 140 C. |
| Example 16-3 | Compound C | 72 | 161.4/192.3 (47.2) | None | No exotherm, Tg = 38 C. |
| Example 16-4 | Compound D | 76 | 62.3/105.5 (11.0) | 163.3/184.9 (65.4) | No exotherm, Tg = 58 C. |

PHR = parts of hardener per 100 parts resin solution

As can be seen by the data in Table 11, the novel hardeners of the invention cure novolac resins, and provide the ability to adjust the cured polymer Tg over a broad range.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A compound of formula III-1:

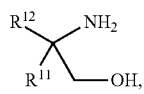

III-1 wherein
$R^{11}$ is an unsubstituted linear $C_2$-$C_{17}$ alkyl;
$R^{12}$ is an unsubstituted linear $C_1$-$C_8$ alkyl,
or $R^{11}$, $R^{12}$, and the carbon to which they are attached form a $C_9$-$C_{11}$ cycloalkyl ring;
provided that
when $R^{12}$ is unsubstituted linear $C_1$-$C_8$ alkyl, the total number of carbons in $R^{11}$ and $R^{12}$, together with the carbon to which they are attached, is 6 to 18; and
the compound is not 2-amino-2-methyl-1-hexanol, 2-amino-2-ethyl-1-hexanol, 2-amino-2-methyl-1-octanol, 2-amino-2-butyl-1-hexanol, 2-amino-2-methyl-1-dodecanol, 2-amino-2-methyl-1-tridecanol, 2 amino-2-methyl-1-pentadecanol, or 2-amino-2-hexyl-1-decanol.

2. The compound of claim 1, wherein $R^{12}$ is an unsubstituted linear $C_1$-$C_8$ alkyl.

3. The compound of claim 1, wherein $R^{12}$ is an unsubstituted linear $C_1$-$C_8$ alkyl, and the total number of carbons in $R^{11}$ and $R^{12}$, together with the carbon to which they are attached, is 6 to 10.

4. A compound according to claim 1 selected from the group consisting of 2-amino-2-ethyl-1-pentanol, 2-amino-2-methyl-1-heptanol, 2-amino-2-propyl-1-pentanol, 2-amino-2-ethyl-1-heptanol, 2-amino-2-propyl-1-hexanol, 2-amino-2-methyl-1-nonanol, 2-amino-2-ethyl-1-octanol, 2-amino-2-propyl-1-heptanol, 2-amino-2-methyl-1-decanol, 2-amino-2-ethyl-1-nonanol, 2-amino-2-propyl-1-octanol, 2-amino-2-butyl-1-heptanol, 2-amino-2-methyl-1-undecanol, 2-amino-2-ethyl-1-decanol, 2-amino-2-propyl-1-nonanol, 2-amino-2-butyl-1-octanol, 2-amino-2-pentyl-1-heptanol, 2-amino-2-ethyl-1-undecanol, 2-amino-2-propyl-1-decanol, 2-amino-2-butyl-1-nonanol, 2-amino-2-pentyl-1-octanol, 2-amino-2-ethyl-1-dodecanol, 2-amino-2-propyl-1-undecanol, 2-amino-2-butyl-1-decanol, 2-amino-2-pentyl-1-nonanol, 2-amino-2-hexyl-1-octanol, 2-amino-2-methyl-1-tetradecanol, 2-amino-2-ethyl-1-tridecanol, 2-amino-2-propyl-1-dodecanol, 2-amino-2-butyl-1-undecanol, 2-amino-2-pentyl-1-decanol, 2-amino-2-hexyl-1-nonanol, 2-amino-2-ethyl-1-tetradecanol, 2-amino-2-propyl-1-tridecanol, 2-amino-2-butyl-1-dodecanol, 2-amino-2-pentyl-1-undecanol, 2-amino-2-heptyl-1-nonanol, 2-amino-2-methyl-1-hexadecanol, 2-amino-2-ethyl-1-pentadecanol, 2-amino-2-propyl-1-tetradecanol, 2-amino-2-butyl-1-tridecanol, 2-amino-2-pentyl-1-dodecanol, 2-amino-2-hexyl-1-undecanol, 2-amino-2-heptyl-1-decanol, 2-amino-2-methyl-1-heptadecanol, 2-amino-2-ethyl-1-hexadecanol, 2-amino-2-propyl-1-pentadecanol, 2-amino-2-butyl-1-tetradecanol, 2-amino-2-pentyl-1-tridecanol, 2-amino-2-hexyl-1-dodecanol, 2-amino-2-heptyl-1-undecanol, 2-amino-2-octyl-1-decanol, 2-amino-2-methyl-1-octadecanol, 2-amino-2-ethyl-1-heptadecanol, 2-amino-2-propyl-1-hexadecanol, 2-amino-2-butyl-1-pentadecanol, 2-amino-2-pentyl-1-tetradecanol, 2-amino-2-hexyl-1-tridecanol, 2-amino-2-heptyl-1-dodecanol, 2-amino-2-octyl-1-undecanol, 1-hydroxymethyl-1-aminocyclononane, 1-hydroxymethyl-1-aminocyclodecane, and 1-hydroxymethyl-1-aminocycloundecane.

\* \* \* \* \*